(12) United States Patent
Koo et al.

(10) Patent No.: US 10,369,089 B2
(45) Date of Patent: Aug. 6, 2019

(54) IRON OXIDE NANOPARTICLES AND METHODS OF USE THEREOF

(71) Applicant: THE TRUSTEES OF THE UNIVERSITY OF PENNSYLVANIA, Philadelphia, PA (US)

(72) Inventors: Hyun Koo, Philadelphia, PA (US); Lizeng Gao, Philadelphia, PA (US); David Cormode, Philadelphia, PA (US); Pratap Naha, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/550,267

(22) PCT Filed: Feb. 12, 2016

(86) PCT No.: PCT/US2016/017858
§ 371 (c)(1),
(2) Date: Aug. 10, 2017

(87) PCT Pub. No.: WO2016/130985
PCT Pub. Date: Aug. 18, 2016

(65) Prior Publication Data
US 2018/0028417 A1 Feb. 1, 2018

Related U.S. Application Data

(60) Provisional application No. 62/115,968, filed on Feb. 13, 2015.

(51) Int. Cl.
*A61K 8/19* (2006.01)
*A01N 59/16* (2006.01)
(Continued)

(52) U.S. Cl.
CPC ............... *A61K 8/19* (2013.01); *A01N 59/16* (2013.01); *A61K 8/0245* (2013.01); *A61K 8/20* (2013.01);
(Continued)

(58) Field of Classification Search
CPC ........................................................ A61K 8/22
See application file for complete search history.

(56) References Cited

U.S. PATENT DOCUMENTS

| | | | |
|---|---|---|---|
| 2010/0233224 A1* | 9/2010 | Ramadurai | A01N 25/28 424/420 |
| 2013/0189375 A1 | 7/2013 | Zhao et al. | |
| 2014/0234429 A1 | 8/2014 | Mahmoudi et al. | |

FOREIGN PATENT DOCUMENTS

WO    WO 2016/007629 A2    1/2016

OTHER PUBLICATIONS

Taylor et al , "The Use of Superparamagnetic Nanoparticles for Prosthetic Biofilm Prevention", International Journal of Nanomedicine , vol. 4 (Aug. 11, 2009), pp. 145-152 (Year: 2009).*

(Continued)

*Primary Examiner* — Carlos A Azpuru
(74) *Attorney, Agent, or Firm* — Baker Botts L.L.P.

(57) ABSTRACT

The presently disclosed subject matter relates to iron oxide nanoparticle compositions and formulations thereof for: (1) the treatment and elimination of biofilms; (2) the prevention of biofilm formation; (3) biofilm extracellular matrix degradation; (4) the inhibition of bacterial viability and growth within the biofilm; and (5) the prevention of tooth or apatitic demineralization. In particular, the presently disclosed subject matter provides a composition for the prevention and treatment of an oral disease (e.g., dental caries) that includes one or more iron oxide nanoparticles and hydrogen peroxide.

20 Claims, 26 Drawing Sheets

(51) Int. Cl.

| | | |
|---|---|---|
| A61K 33/26 | (2006.01) | |
| A61K 33/40 | (2006.01) | |
| A61Q 11/00 | (2006.01) | |
| A61K 9/14 | (2006.01) | |
| A61K 9/51 | (2006.01) | |
| A61K 47/69 | (2017.01) | |
| A61K 8/02 | (2006.01) | |
| A61K 8/20 | (2006.01) | |
| A61K 8/22 | (2006.01) | |
| A61K 8/66 | (2006.01) | |
| A61K 8/73 | (2006.01) | |
| A61K 8/24 | (2006.01) | |
| A61K 8/21 | (2006.01) | |
| A61K 9/00 | (2006.01) | |

(52) U.S. Cl.
CPC ............... *A61K 8/21* (2013.01); *A61K 8/22* (2013.01); *A61K 8/24* (2013.01); *A61K 8/66* (2013.01); *A61K 8/73* (2013.01); *A61K 9/14* (2013.01); *A61K 9/5161* (2013.01); *A61K 33/26* (2013.01); *A61K 33/40* (2013.01); *A61K 47/6923* (2017.08); *A61Q 11/00* (2013.01); *A61K 9/006* (2013.01); *A61K 9/0063* (2013.01); *A61K 2800/413* (2013.01); *A61K 2800/624* (2013.01); *A61K 2800/882* (2013.01); *A61K 2800/92* (2013.01); *Y02A 50/471* (2018.01); *Y02A 50/473* (2018.01)

(56) References Cited

OTHER PUBLICATIONS

Nanoparticle Mouthwash May Reduce Tooth Plaque, AzoNano, 2018 (Year: 2018).*
Liu et al, Topical Ferumoxytol Nanoparticles Disrupt Biofilms and Prevent Tooth Decay In Vivo Via Intrinsic Catalytic Activity, Nature Communications, 9(1), 2018. (Year: 2018).*
Agarwala et al., "Comparative Study of Antibiofilm Activity of Copper Oxide and Iron Oxide Nanoparticles Against Multidrug Resistant Biofilm Forming Uropathogens," Indian Journal of Microbiology, 54(3):365-368 (2014).
Allaker et al., "Nanoparticles and the control of oral infections," Int J Antimicrob Agents, 43:95-104 (2014).
Allaker, "The Use of Nanoparticles to Control Oral Biofilm Formation," Journal of Dental Research, 89(11):1175-1186 (2010).
Ambatipudi et al., "Human Common Salivary Protein 1 (CSP-1) Promotes Binding of *Steptococcus mutans* to Experimental Salivary Pellicle and Glucans Formed on Hydroxyapatite Surface," J Proteome Res, 9(12):6605-6614 (2010).
Arciola et al, "Biofilm-Based Implant Infections in Orthopaedics," Adv Exp. Med Biol., 830:29-46 (2015).
Arthur et al., "Enamel Carious Lesion Development in Response to Sucrose and Fluoride Concentrations and to Time of Biofilm Formation: An Artificial-Mouth Study," Journal of Oral Diseases, Article ID 348032 (2014), 8 pages.
Banas et al., "Glucan-Binding Proteins of the Oral Streptococci," Crit. Rev Oral Biol. Med, 14(2):89-99 (2003).
Bin Asif et al., "Visible light functioning photocatalyst based on Al2O3 doped Mn3O4 nanomaterial for the degradation of organic toxin," Nanoscale Research Letters 10:355 (2015).
Bowen et al., "Biology of *Streptococcus mutans*-Derived Glucosyltransferases: Role in Extracellular Matrix Formation of Cariogenic Biofilms," Caries Res, 45:69-86 (2011).
Bowen, "Rodent model in caries research," Odontology, 101:9-14 (2013).
Cormode et al., "Nanoparticle contrast agents for computed tomography: a focus on micelles," Contrast Media Mol. Imaging, 9:37-52 (2014).
Cury et al., "Extraction and purification of total RNA from *Streptococcus mutans* biofilms," Analytical Biochemistry, 365:208-214 (2007).
Cury et al., "In situ Relationship between Sucrose Exposure and the Composition of Dental Plaque," Caries Research, 31:356-360 (1997).
Delbem et al., "Effect of Iron II on Hydroxyapatite Dissolution and Precipitation in vitro," Caries Res, 46:481-487 (2012).
Deng et al., "Monodisperse Magnetic Single-Crystal Ferrite Microspheres," Angew. Chem. Int. Ed. Engl., 44:2782-2785 (2005).
Extended Search Report dated Jun. 20, 2018 in Application No. EP 16750009.
Falsetta et al., "Symbiotic relationship between *Streptococcus mutans* and *Candida albicans* synergizes the virulence of plaque-biofilms in vivo," Infect Immun., (2014).
Fan et al., "Human ferritin for tumor detection and therapy," WIREs Nanomedicine and Nanobiotechnology, 5:287-298 (2013).
Fejerskov et al., "The Effect of Sucrose on Plaque pH in the Primary and Permanent Dentition of Caries-inactive and -active Kenyan Children," J Dent Res, 71(1):25-31 (1992).
Flemming et al., "The Biofilm Matrix," Nat Rev Microbiol, 8:623-633 (2010).
Gao et al., "Intrinsic peroxidase-like activity of ferromagnetic nanoparticles," Nature Nanotechnology, 2:577-583 (2007).
Gao et al., "Synthetic micro/nanomotors in drug delivery," Nanoscale, 6:10486-10494 (2014).
Gregoire et al., "Role of Glucosyltransferase B in Interactions of Candida albicans with *Streptococcus mutans* and with an Experimental Pellicle on Hydroxyapatite Surfaces," Applied Environ Microbiol, 77(18):6357-6367 (2011).
Hall-Stoodley et al., "Bacterial Biofilms: From the Natural Environment to Infectious Diseases," Nat Rev Microbiol, 2:95-108 (2004).
Hannig et al., "Nanomaterials in preventive dentistry," Nature Nanotechnology 5:565-569 (2010).
Hara et al., "Influence of the Organic Matrix on Root Dentine Erosion by Citric Acid," Caries Research, 39:134-138 (2005).
Hara et al., "Novel in-situ longitudinal model for the study of dentifrices on dental erosion—abrasion," European J. Oral Sci 122:161-167 (2014).
Horev et al., "pH-activated Nanoparticles for Controlled Topical Delivery of Farnesol to Disrupt Oral Biofilm Virulence," ACS Nano, 9(3):2390-2404 (2015).
Hudson et al., "Bare magnetic nanoparticles: sustainable synthesis and applications in catalytic organic transformations," Green Chemistry, 16:4493-4505 (2014).
International Search Report dated Jun. 24, 2016 in International Application No. PCT/US16/17858.
Katsarelis et al., "Infection and Medication-related Osteonecrosis of the Jaw," Journal of Dental Research 94(4):534-539 (2015).
Klein et al., "An Analytical Tool-box for Comprehensive Biochemical, Structural and Transcriptome Evaluation of Oral Biofilms Mediated by Mutans Streptococci," J Vis Exp. 47:e2512 (2011).
Klein et al., "Molecular approaches for viable bacterial population and transcriptional analyses in a rodent model of dental caries," Mol. Oral Microbiol, 27(5):350-361 (2012).
Kong et al., "Mineralization of calcium phosphate in reverse microemulsion," Curr Appl Phys, 5:519-521 (2005).
Koo et al., "Apigenin and tt-Farnesol with Fluoride Effects on S. mutans Biofilms and Dental Caries," J Dent Res, 84(11):1016-1020 (2005).
Koo et al., "Effects of Compounds Found in Propolis on *Streptococcus mutans* Growth and on Glucosyltransferase Activity," Antimicrob Agents Chemother, 46(5):1302-1309 (2002).
Koo et al., "Exopolysaccharides Produced by *Streptococcus mutans* Glucosyltransferases Modulate the Establishment of Microcolonies within Multispecies Biofilms," J Bacteriol, 192(12):3024-3032 (2010).
Koo et al., "Inhibition of *Streptococcus mutans* biofilm accumulation and polysaccharide production by apigenin and tt-farnesol," J Antimicrob Chemother, 52:782-789 (2003).
Koo et al., "The Exopolysaccharide Matrix: A Virulence Determinant of Cariogenic Biofilm," J Dent Res, 92(12):1065-1073 (2013).

(56) References Cited

OTHER PUBLICATIONS

Kopec et al., "Structural aspects of glucans formed in solution and on the surface of hydroxyapatite," Glycobiology, 7(7):929-934 (1997).
Larson, "Merits and Modifications of Scoring Rat Dental Caries by Keyes' Method," Animal Models in Cariology: Proceedings of a Symposium and Workshop on Animal Models in Cariology, pp. 195-203, Apr. 21-23, 1980.
Lebeaux et al., "Biofilm-Related Infections: Bridging the Gap between Clinical Management and Fundamental Aspects of Recalcitrance toward Antibiotics," Microbiol Mol Biol Rev, 78(3):510-543 (2014).
Liao et al., "Composite three-dimensional woven scaffolds with interpenetrating network hydrogels to create functional synthetic articular cartilage," Adv Funct Mater, 23(47):5833-5839 (2013).
Liu et al., "Pectin/poly(lactide-co-glycolide) composite matrices for biomedical applications," Biomaterials, 25:3201-3210 (2004).
Mercier et al., Effect of growth phase and pH on the in vitro activity of a new glycopeptide, oritavancin (LY333328), against *Staphylococcus aureus* and *Enterococcus faecium*, J Antimicrob Chemother, 50:19-24 (2002).
Mohamed et al., "Enhanced nanocatalysts," Mat Sci Eng R, 73:1-13 (2012).
Naha et al., "Dextran coated bismuth-iron oxide nanohybrid contrast agents for computed tomography and magnetic resonance imaging," J Mater Chem B Mater Biol. Med, 2(46):8239-8248 (2014).
Pecharki et al., "Effect of Sucrose Containing Iron (II) on Dental Biofilm and Enamel Demineralization in situ," Caries Res, 39:123-129 (2005).
Poschet et al., "Hyperacidification in cystic fibrosis: links with lung disease and new prospects for treatment," Trends Mol. Med, 8(11):512-519 (2002).
Ribeiro et al., "The effect of iron on *Streptococcus mutans* biofilm and on enamel demineralization," Braz Oral Res., 26(4):300-305 (2012).
Rosalen et al., "Effects of Copper, Iron and Fluoride Co-Crystallized With Sugar on Caries Development and Acid Formation in Desalivated Rats," Arch Oral Biol., 41(11):1003-1010 (1996).
Subbiahdoss et al., "Magnetic targeting of surface-modified superparamagnetic iron oxide nanoparticles yields antibacterial efficacy against biofilms of gentamicin-resistant staphylococci," Acta Biomaterialia, 8:2047-2055 (2012).
Sun et al., "Preparation and Properties of Nanoparticles of Calcium Phosphates with Various Ca/P Ratios," J Res Natl Inst Stand Technol., 115:243-255 (2010).
Tassa et al., "Dextran-Coated Iron Oxide Nanoparticles: a Versatile Platform for Targeted Molecular Imaging, Molecular Diagnostics and Therapy," Acc Chem Res., 44(10):842-852 (2011).
Taylor et al., "The use of superparamagnetic nanoparticles for prosthetic biofilm prevention," International Journal of Nanomedicine, 4:145-152 (2009).
Triantis et al., "Sensitized chemiluminescence of luminol catalyzed by colloidal dispersions of nanometer-sized ferric oxides," Chem Eng J, 144:483-488 (2008).
Tsumori et al., "Combination of Mutanase and Dextranase Effectively Suppressed Formation of Insoluble Glucan Biofilm by Cariogenic Streptococci," Interface Oral Health Science, pp. 215-217 (2011).
Wang et al., "One-step synthesis of easy-recycling $TiO_2$-rGO nanocomposite photocatalysts with enhanced photocatalytic activity," Applied Catalysis B: Environmental, 132-133:452-459 (2013).
Wang et al., "The impact of quantitative imaging in medicine and surgery: Charting our course for the future," Quant Imaging Med Surg, 1:1-3 (2011).
Xiao et al., "The Exopolysaccharide Matrix Modulates the Interaction between 3D Architecture and Virulence of a Mixed-Species Oral Biofilm," PLoS Pathog, 8(4):e1002623 (2012).
Zero et al., "An Improved Intra-oral Enamel Demineralization Test Model for the Study of Dental Caries," Journal of Dental Research, 71(Spec Iss):871-878 (1992).

\* cited by examiner

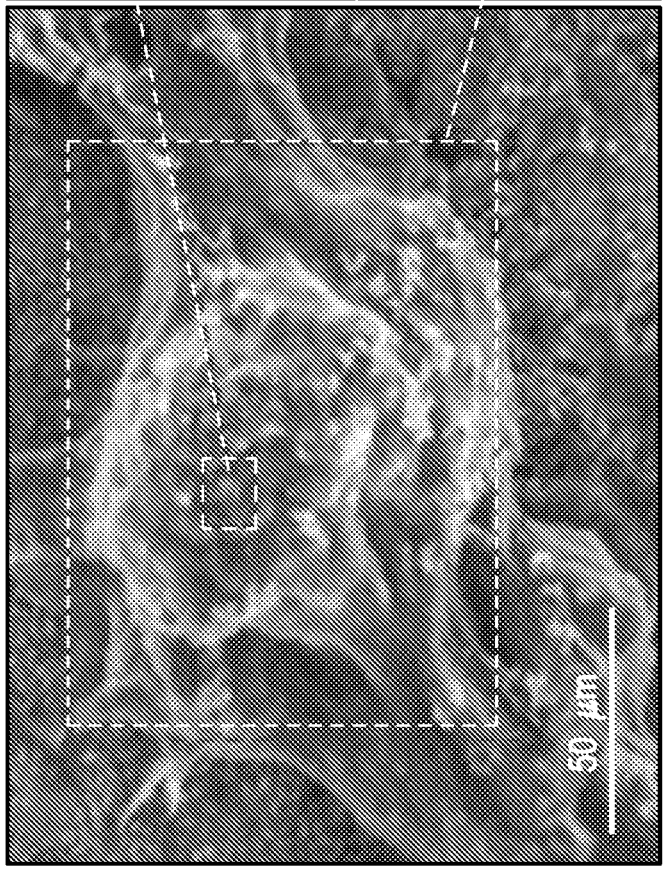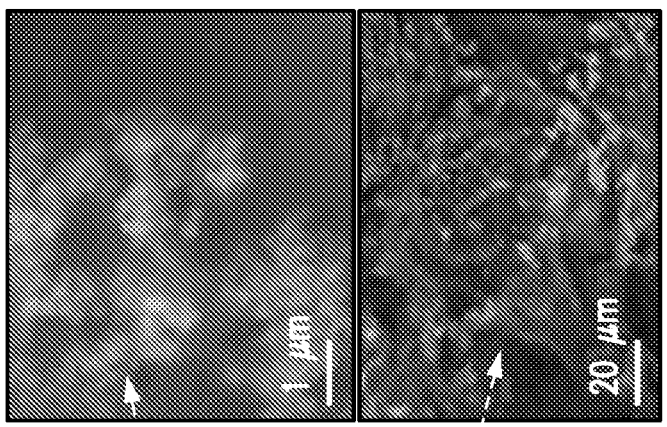
FIG. 4A
FIG. 4B
FIG. 4C

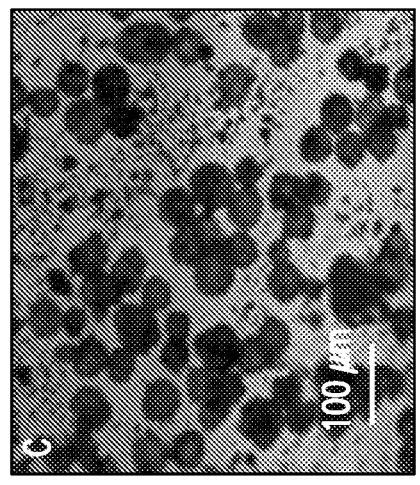
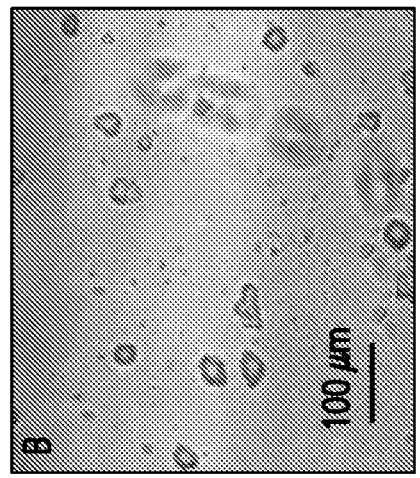
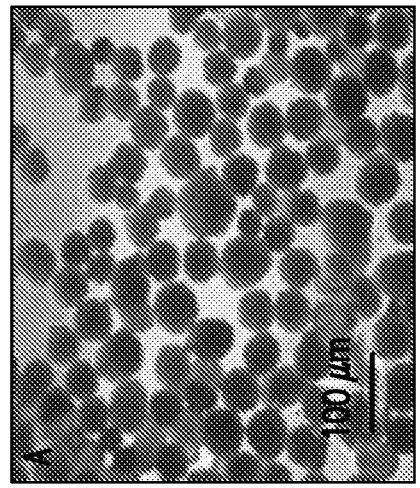
FIG. 7C
FIG. 7B
FIG. 7A

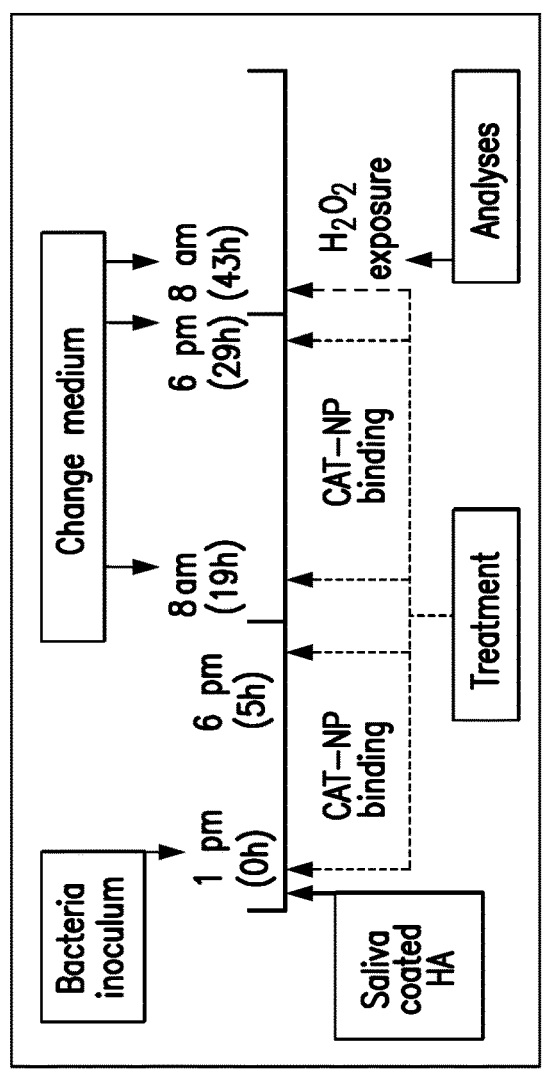
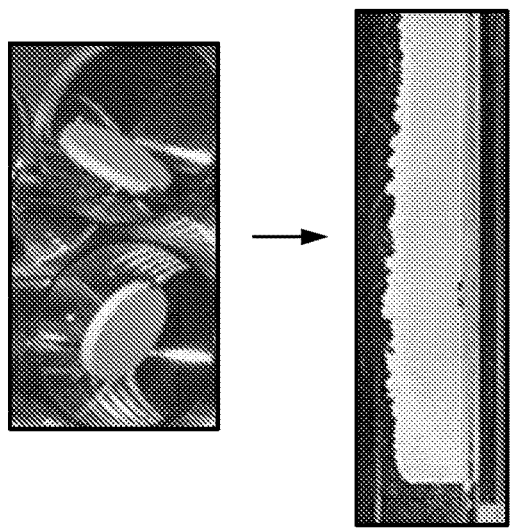
FIG. 9A
FIG. 9B

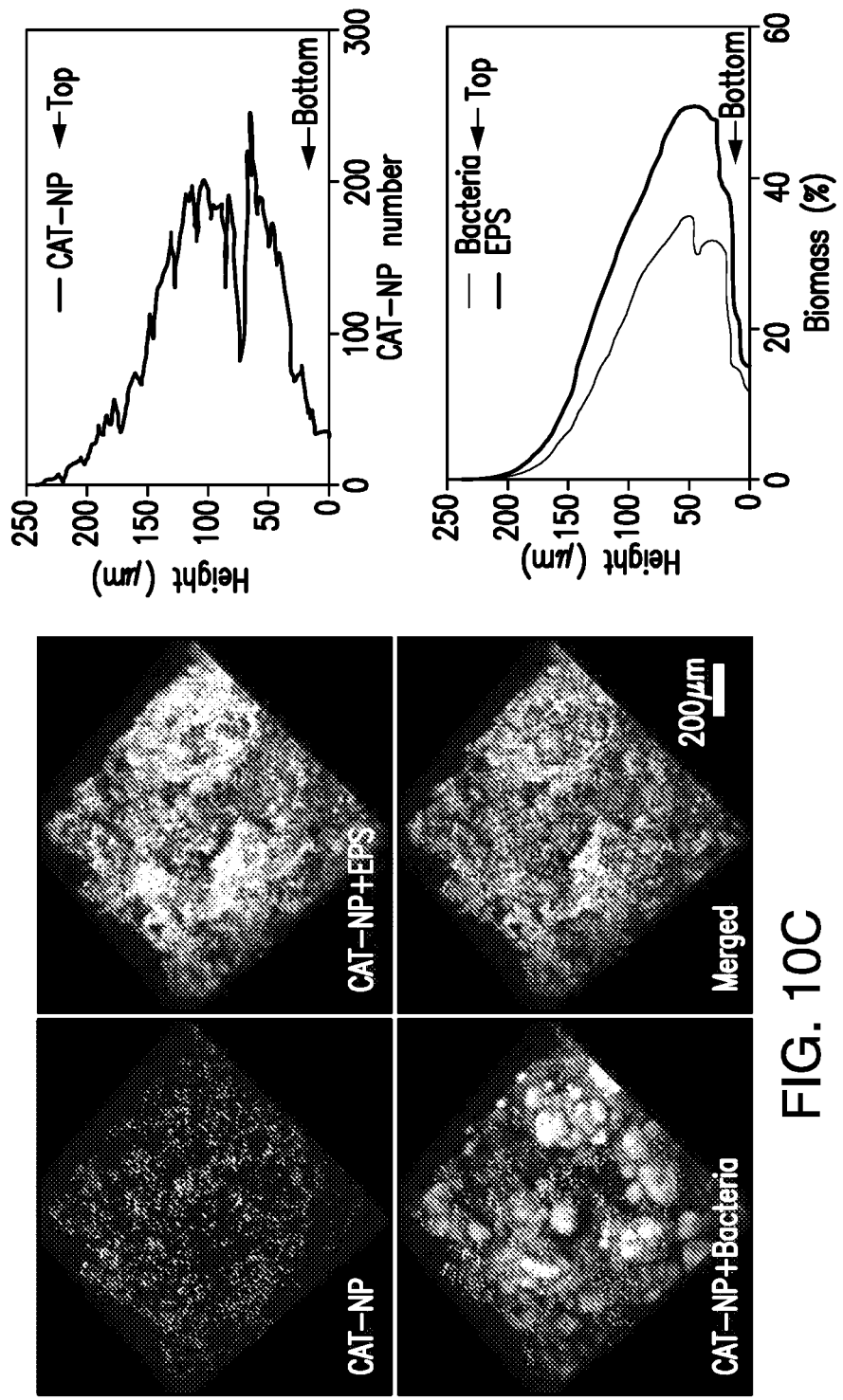

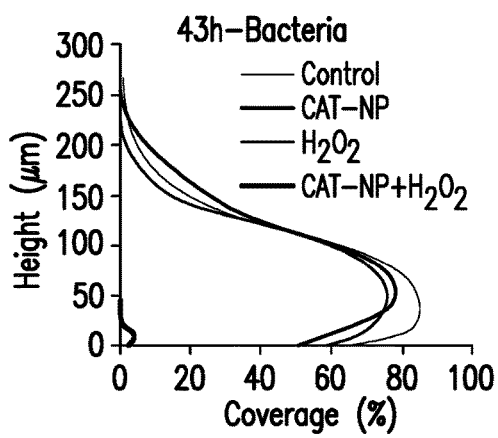
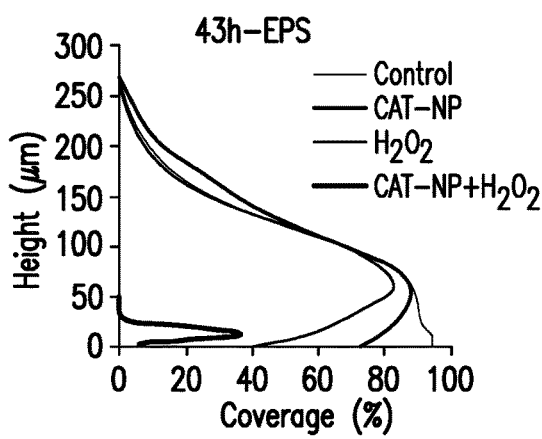
FIG. 15A  FIG. 15B
| Biofilm 43 h | COMSTAT analysis | | |
|---|---|---|---|
| | Total Biovolume ($\mu m^3/\mu m^2$) | Cell Biovolume ($\mu m^3/\mu m^2$) | EPS Biovolume ($\mu m^3/\mu m^2$) |
| Control | 204.2 ± 17.4 | 98.9 ± 6.8 | 105.3 ± 11.1 |
| CAT-NP | 229.5 ± 11.3 | 113.1 ± 12.3 | 116.5 ± 6.3 |
| $H_2O_2$ | 194.8 ± 7.8 | 89.8 ± 6.4 | 105.0 ± 2.3 |
| CAT-NP+$H_2O_2$ | 2.6 ± 0.2 | 1.7 ± 0.1 | 0.9 ± 0.3 |
FIG. 15C

IRON OXIDE NANOPARTICLES AND METHODS OF USE THEREOF

CROSS-REFERENCE TO RELATED APPLICATIONS

This application is a U.S. National Stage Patent Application under 35 U.S.C. § 371 of International Application No. PCT/US2016/017858, filed on Feb. 12, 2016, which claims priority to U.S. Provisional Application Ser. No. 62/115,968, filed on Feb. 13, 2015, the contents of which are incorporated by reference herein in its their entirety.

GRANT INFORMATION

This invention was made with government support under grant numbers DE018023 and EB102165 awarded by the National Institutes of Health. The government has certain rights in the invention.

BACKGROUND

Biofilms are structured communities of microorganisms that can be firmly attached to a surface and enmeshed in a self-produced three-dimensional (3D) extracellular matrix. Biofilms can form on living or non-living surfaces and can exist in natural and industrial settings. For example, biofilms can contaminate man-made aquatic systems such as cooling towers, pools and spas. In the industrial setting, biofilms can develop on the interiors of pipes that can lead to clogs and corrosion. Biofilms can also be formed within implanted medical tubing and medical devices as well as within the human body (mucosal surfaces), which can lead to infections in patients. Similarly, biofilms can develop within the oral cavity and result in oral diseases such as dental caries. The extracellular matrices of such biofilms contain polymeric substances, such as exopolysaccharides (EPS). The matrix produced by microorganisms can provide an essential scaffold for biofilm assembly. Additionally, it can promote microbial adhesion and cohesion while hindering diffusion, thereby making biofilms extremely difficult to treat or remove from surfaces.

In the oral cavity context, EPS, which form the core of the matrix, are the prime building blocks of cariogenic, i.e., caries-producing, biofilms (also known as dental plaques). This EPS-rich extracellular matrix promote the formation of highly cohesive and adherent biofilms as well as hinder diffusion that helps create highly acidic microenvironments within the biofilm. Such high acidity can enhance the survival and growth of cariogenic flora, and can further induce the production of the polymeric extracellular matrix, thereby ensuring pathogenic biofilm accretion while promoting acid-dissolution of the adjacent tooth enamel. This extracellular matrix also contributes to the difficulty in the elimination of microbial biofilms within the oral cavity and human body, as well as on biomaterials, e.g., implants and medical devices, by antibodies, antibiotics and immune cells, which are unable to penetrate the dense extracellular matrix to kill the embedded microorganisms. Furthermore, the acidic pH of the EPS-rich extracellular matrix can reduce efficacy of some antibiotics.

Certain approaches for controlling cariogenic biofilms are restricted to standard bactericidal agents, such as chlorhexidine (CHX), rather than targeting matrix disruption. Although capable of killing planktonic *Streptococcus mutans*, CHX can be less effective against biofilms and is not suitable for daily therapeutic use due to adverse effects such as calculus formation and tooth staining. In addition, chemical and biological agents can have some disadvantages, such as discoloration of teeth or tongue, desquamation and soreness of oral mucosa, objectionable taste, toxicity and can also cause an imbalance of the complex oral flora.

Certain antimicrobial nanoparticles have been explored as potential approaches to disrupt oral biofilms. However, many have limitations similar to those seen with CHX. Metal nanoparticles, such as silver and copper nanoparticles, have shown broad antibacterial activity. However, these agents do not target the matrix and may not work well under acidic microenvironments, resulting in limited anti-biofilm efficacy. The development of effective therapies to control oral biofilms is also affected by the lack of retention and bioactivity of topically introduced agents in the mouth. Therefore, there is a need in the art for compositions that can effectively treat biofilms in general by simultaneously degrading the matrix and killing embedded bacteria, including, but not limited to those that can appear in the oral cavity.

SUMMARY

The presently disclosed subject matter provides iron oxide nanoparticle compositions and formulations thereof for: (1) the treatment and/or elimination of biofilms; (2) the prevention of biofilm formation; (3) biofilm extracellular matrix degradation; (4) the inhibition of bacterial viability and growth within the biofilm; and/or (5) the prevention of tooth or apatitic demineralization.

In certain embodiments, the present disclosure provides compositions for the prevention and/or treatment of biofilm-associated diseases, e.g., oral disease, that include one or more iron nanoparticles and hydrogen peroxide. In certain embodiments, the one or more iron nanoparticles are conjugated to one or more enzymes. For example, and not by way of limitation, the one or more iron nanoparticles are conjugated to matrix degrading and/or peroxide producing enzymes. In certain embodiments, the oral disease is dental caries. In certain embodiments, the one or more iron nanoparticles can have a diameter of about 1 nm to about 1000 nm. In certain embodiments, the one or more iron nanoparticles have a polymeric coating. In certain embodiments, the one or more iron nanoparticles do not have a polymeric coating.

The present disclosure further provides compositions for the prevention and/or treatment of a biofilm that include one or more iron nanoparticles and hydrogen peroxide. In certain embodiments, the one or more iron nanoparticles are conjugated to one or more matrix degrading and/or peroxide producing enzymes. In certain embodiments, the one or more iron nanoparticles can have a diameter of about 1 nm to about 1000 nm. In certain embodiments, the composition further includes fluoride. In certain embodiments, the one or more nanoparticles are doped with a metal such as, but not limited to, manganese, cobalt, calcium, nickel, magnesium strontium, barium, scandium, titanium, vanadium, chromium, zinc, aluminum, yttrium, zirconium, niobium, molybdenum, ruthenium, rhodium, palladium, hafnium, tantalum, tungsten, rhenium, osmium, iridium, platinum, copper or a combination thereof. In certain embodiments, the one or more iron nanoparticles do not have or have a polymeric coating. In certain embodiments, the polymeric coating includes dextran. In certain embodiments, the biofilm is generated by *S. mutans, P. aeruginosas, E. coli, E faecalis, B. subtilis, S. aureus, Vibrio cholerae, Candida albicans* or a combination thereof. The biofilm can be present on a surface of a tooth, a mucosal surface, a medical device, an industrial material, a naval material, skin, an interior of a tooth (e.g., endodontic canal), lung (e.g., cystic fibrosis) or the urinary tract.

The present disclosure provides methods for the prevention, elimination and/or treatment of an oral disease that include administering to a subject an effective amount of a composition that includes one or more iron nanoparticles. In certain embodiments, the concentration of the iron nanoparticles within the composition is from about 0.1 to about 1.0 mg/ml. In certain embodiments, the method can further include administering to the subject an effective amount of hydrogen peroxide. In certain embodiments, the hydrogen peroxide is administered in a solution that includes hydrogen peroxide at a concentration from about 0.1% to about 3.0%. In certain embodiments, the method can further include administering to the subject an effective amount of fluoride. In certain embodiments, the one or more iron nanoparticles are conjugated to matrix degrading and/or peroxide producing enzymes. In certain embodiments, the composition can further include fluoride, hydrogen peroxide, calcium phosphate, copper, sodium percarbonate or combinations thereof. In certain embodiments, the one or more iron nanoparticles can have a diameter of about 1 nm to about 1000 nm. In certain embodiments, the one or more iron nanoparticles do not have or have a polymeric coating. In certain embodiments, the one or more iron nanoparticles have a polymeric coating.

The present disclosure provides methods for the prevention, elimination and/or treatment of a biofilm that includes contacting a surface having a biofilm with an effective amount of a composition that includes one or more iron nanoparticles. In certain embodiments, the biofilm is present on the surface of a tooth surface, a mucosal tissue surface, a soft-tissue surface, skin, an apatitic surface, an implant surface, a medical device surface, an industrial surface, a surface of a naval vessel, a surface of a watercraft, a ship hull or a pipe surface. In certain embodiments, the method can further include contacting the surface with a solution that includes hydrogen peroxide, where the one or more iron nanoparticles catalyze hydrogen peroxide to form one or more free radicals that can degrade the biofilm matrix and/or kill the embedded bacteria. In certain embodiments, the one or more free radicals simultaneously degrade the biofilm matrix and kill the embedded bacteria.

In certain embodiments, a method for the prevention of bacterial growth in a biofilm includes contacting a surface having a biofilm with an effective amount of a composition that includes one or more iron nanoparticles, where the one or more iron nanoparticles bind to the surface and release iron to inhibit bacterial growth within the biofilm. The present disclosure further provides methods for preventing the formation of a biofilm on a surface. In certain embodiments, a method for preventing the formation of a biofilm on a surface can include treating a surface that is at risk for biofilm development with an effective amount of a composition that includes one or more iron nanoparticles. In certain embodiments, the surface can be coated with an effective amount of a composition comprising one or more iron nanoparticles. In certain embodiments, the composition can include one or more iron nanoparticles and hydrogen peroxide and/or sodium percarbonate. For example, and not by way of limitation, such at risk surfaces include a tooth surface, a mucosal surface, an implant surface, a device surface and a pipe surface.

The presently disclosed subject matter further provides methods for preventing tooth or hydroxylapatite (HA) demineralization. In certain embodiments, a method for the prevention of tooth demineralization can include contacting a tooth-enamel or an apatitic (e.g., bone) surface having a biofilm with an effective amount of a composition that includes one or more iron nanoparticles. In certain embodiments, the one or more iron nanoparticles bind to the surface to inhibit and/or prevent enamel or apatitic dissolution.

The present disclosure provides kits for the prevention and/or treatment of a biofilm that includes a first container that includes a composition having one or more iron nanoparticles and second container that includes a hydrogen peroxide solution. In certain embodiments, the kit can include a container that contains a composition that has one or more iron nanoparticles and hydrogen peroxide, where the hydrogen peroxide is inactivated and/or complexed and can become activated and/or released in the mouth or when in contact with water.

BRIEF DESCRIPTION OF THE DRAWINGS

FIG. 2A depicts an EPS matrix (in red) and bacteria (in green) within a mature biofilm. FIG. 2B depicts a close-up view of the cell matrix structural organization that shows EPS holding bacteria together and forming compartmentalized architecture. FIG. 2C depicts an image of the in situ pH of an intact biofilm with highly acidic microenvironments (dotted area).

FIGS. 4A-4C depict images of IO-NP retention on S. mutans biofilms characterized by scanning electron microscopy (SEM). FIG. 4A depicts the morphology of a biofilm treated with IO-NPs. FIG. 4B depicts a close-up view of IO-NPs bound to the biofilm. FIG. 4C depicts an elemental analysis of SEM images showing IO-NP (pink) distribution on the biofilms.

FIG. 5A depicts a graph of the effective killing of S. mutans within a biofilm. FIG. 5B depicts a graph of EPS matrix degradation.

FIG. 6A depicts a graph showing that IO-NPs inhibit bacteria viability under low pH in media containing glucose. FIG. 6B depicts a graph showing iron release from IO-NPs under low pH (below 5.5) at 37° C. FIG. 6C depicts a graph showing that IO-NPs catalyze $H_2O_2$ to quickly generate free radicals under low pH (pH between 4 and 5).

FIGS. 7A-7C depict images showing that IO-NPs reduce hydroxyapatite (HA) demineralization in acidic conditions. FIG. 7A is an image of untreated HA beads. FIG. 7B is an image of HA beads in acidic buffer (pH 4.5). FIG. 7C is an image of HA beads with IO-NPs in acidic buffer, showing the protective effects of IO-NP against HA acid-dissolution.

FIGS. 8A-8B depict images of the CAT-NPs by TEM. FIG. 8C is a graph showing the size distribution of the CAT-NPs (213.3±26.5 nm). FIG. 8D is a graph of CAT-NP activity as determined by the 3,3',5,5'-tetramethylbenzidine (TMB) method. FIG. 8E is a graph of CAT-NP activity as measured by AMPLEX® UltraRed (excitation/emission at 568/581 nm). The data are depicted as mean±s.d.

FIGS. 9A-9B depict an exemplary experimental design and in vitro saliva-coated hydroxyapatite (sHA) biofilm model. FIG. 9A depicts an exemplary biofilm experimental design and topical treatment regimen. FIG. 9B depicts the vertical placement of sHA discs within 24-well plates and the formation of a biofilm on the surface of the sHA discs.

FIGS. 10A-10F depict the retention and catalytic activity of CAT-NPs within biofilms. FIG. 10A depicts the morphology of a biofilm with bound CAT-NPs (arrows). FIG. 10A1 depicts a magnified view of CAT-NPs within the area selected in FIG. 10A. FIG. 10A2 depicts SEM/EDS images showing the distribution of iron (pink) on biofilms. FIG. 10B depicts a graph showing the amount of CAT-NPs bound within a biofilm as determined by measuring iron amounts with ICP-MS. FIG. 10C depicts the spatial distribution of CAT-NPs within a biofilm (EPS (red), bacteria (green), CAT-NP (white) were observed with confocal microscopy). FIG. 10D depicts graphs showing the orthogonal distribution of CAT-NPs across the thickness of a biofilm. FIG. 10E depicts a graph showing the catalytic activity of CAT-NPs within biofilms (inset: images of CAT-NP treated biofilm before and after exposure to $H_2O_2$ and TMB (the blue color indicates free-radical generation via $H_2O_2$ catalysis in situ)). FIG. 10F depicts a graph showing the catalytic activity of CAT-NPs in biofilms at different pHs.

FIG. 13A is a graph showing the viability of S. mutans within CAT-NP treated-biofilms 5 minutes after $H_2O_2$ exposure. FIG. 13B is a graph showing EPS degradation within biofilms 30 min after $H_2O_2$ exposure. FIG. 13C is a graph showing the degradation of insoluble glucans produced by GtfB and soluble glucans from GtfD. FIG. 13D depicts confocal microscopy images showing the dynamics of biofilm disruption after topical treatments with CAT-NP+$H_2O_2$. Biofilms received topical treatment by CAT-NP followed immediately by $H_2O_2$ exposure (CAT-NP+$H_2O_2$) or sodium acetate buffer (CAT-NP alone) twice daily. For biofilms treated with $H_2O_2$ in the absence of CAT-NPs, biofilms were treated with sodium acetate buffer followed immediately by $H_2O_2$ exposure. The control group consisted of biofilms treated with buffer only. Bacterial cells were stained with SYTO 9 (in green) and EPS were labeled with Alexa Fluor 647 (in red). Data are shown as mean±s.d. *$P \leq 0.001$ (vs. control).

FIG. 14A is a graph of the antibacterial activity, as determined by counting the total number of viable cells (colony forming units, CFU). FIG. 14B is a graph of the reduction in the biomass (dry-weight) of the biofilm. The data are depicted as mean±s.d.

FIGS. 15A-15C depict the quantitative analysis of bacteria and EPS biovolumes within treated biofilms. FIG. 15A depicts a graph of the bacteria biovolume within treated biofilms (at 43 h) using COMSTAT. FIG. 15B depicts a graph of the EPS biovolume within treated biofilms (at 43 h) using COMSTAT. FIG. 15C provides a table showing the quantitative analysis of bacteria and EPS biovolumes within treated biofilms at 43 h using COMSTAT. The data are depicted as mean±s.d.

FIG. 16A depicts images of teeth from rats that were treated as noted. Green arrows indicate initial lesion formation where areas of the enamel were demineralized and became white; blue arrows show moderate carious lesions where areas of enamel were white-opaque or damaged. In some areas, the enamel was eroded leading to cavitation, which is the most severe carious lesion (red arrows). FIG. 16B depicts graphs showing scores recorded as stages and extent of carious lesion severity according to Larson's modification of Keyes' scoring system: Initial lesion (surface enamel white); moderate lesion (enamel white-opaque); and extensive (cavitation with enamel eroded and underlying dentin exposed). Data are shown as mean±s.d. *$P \leq 0.001$ (vs. control); ** $P \leq 0.05$ (vs. control); δ indicates no detection.

FIG. 18A depicts images of untreated sHA beads (80 μm diameter), sHA beads in acidic buffer (pH 4.5) and sHA beads with CAT-NP in acidic buffer. FIG. 18B depicts an exemplary graph showing the amount of remaining sHA after acid-dissolution. FIG. 18C depicts an exemplary graph showing the amount of iron released from CAT-NPs after incubation at pH 4 or pH 7. The data are depicted as mean±s.d.

FIG. 19A depicts a graph showing the kinetics of the catalytic activities (using the TMB method) of different types of CAT-NPs (at the same amount): CAT-NPs, CAT-NPs coated with dextran and CAT-NPs coated with dextran and doped with manganese (Mn). FIG. 19B depicts a graph showing the catalytic activity of CAT-NPs as compared to the catalytic activity of modified CAT-NPs. The data (activity relative to unmodified CAT-NP) are depicted as mean±s.d., and clearly demonstrate enhancement of catalytic activity due to modifications.

FIG. 22A is an image showing an IO-NP-treated biofilm before and after exposure to $H_2O_2$ and TMB; blue color indicates ROS generation via $H_2O_2$ catalysis in situ. FIG. 22B is a graph showing the amount of free radicals generated, as measured at $OD_{652}$.

FIG. 23A is a graph depicting cell viability of BJ5ta cells after incubation with iron oxide nanoparticles for 24 hours. FIG. 23B is a graph depicting cell viability of HepG2 cells after incubation with iron oxide nanoparticles for 24 hours. The data show no toxic effects against cells.

DETAILED DESCRIPTION

Figure 1:
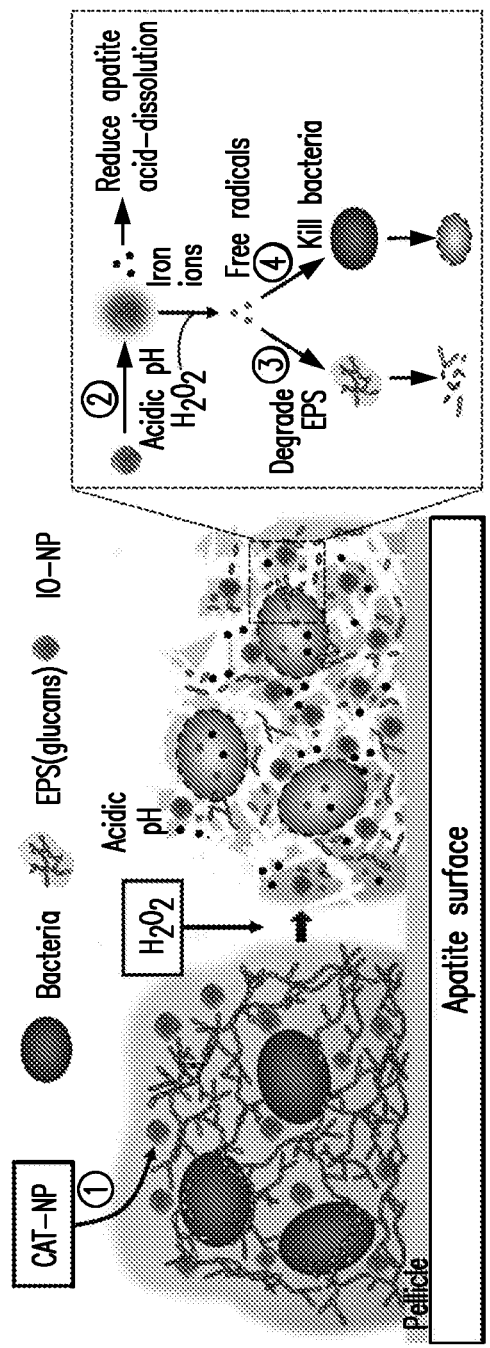
FIG. 1 depicts a schematic of a proposed model for biofilm elimination/disruption by the activation of $H_2O_2$ by catalytic nanoparticles (CAT-NPs) in situ.

The presently disclosed subject matter provides iron oxide nanoparticle (IO-NP) compositions and formulations thereof for the elimination of biofilms, the prevention of biofilm formation, matrix degradation and/or the inhibition of microorganism viability and growth within the biofilm. The presently disclosed subject matter further provides methods of using the compositions and formulations of the present disclosure in the treatment of oral diseases as well as for industrial and other medical applications.

As used herein, a "biofilm" includes an extracellular matrix and one or more microorganisms such as, but not limited to, bacteria, fungi, algae and protozoa, which is attached to a surface. For example, but not by way of limitation, such surfaces can include tooth, mucosal, apatitic, bone and abiotic (e.g., implant, dentures, pipes, etc.) surfaces. Biofilms can form on living or non-living surfaces and can exist in natural and industrial settings.

Biofilms that can be prevented, eliminated and/or treated by the compositions and/or formulations of the present disclosure include, but are not limited to, biofilms present within the oral cavity, e.g., on the surface of teeth, on the surface of mucosal/soft-tissues such as gingivae/periodontium and inside a tooth canal (e.g., endodontic canal). In certain embodiments, biofilms that can be prevented, eliminated and/or treated by the compositions and/or formulations of the present disclosure include biofilms on the urinary tract, lung, gastrointestinal tract, on and/or within chronic wounds, and present on the surface (e.g., implants) and within medical devices and medical lines, e.g., catheters, medical instruments and medical tubing. Additional non-limiting examples of biofilms include biofilms present within industrial equipment and materials, e.g., pipes for water, sewage, oil or other substances. In certain embodiments, compositions and/or formulations of the present disclosure can be used to treat or clean the hulls of ships and other watercraft.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and/or up to 1% of a given value.

As noted above, the compositions of the present disclosure can be used to reduce the growth and/or inhibit the viability of one or more microorganisms, e.g., bacteria in a biofilm. For example, and not by way of limitation, the bacteria can include *Streptococcus mutans* (*S. mutans*), *Streptococcus sobrinus, Streptococcus sanguis (sanguinis), Streptococcus gordonii, Streptococcus oralis, Streptococcus mitis, Actinomyces odontolyticus, Actinomyces viscosus, Aggregatibacter actinomycetemcomitans, Lactobacillus* spp., *Porphyromonas gingivalis, Prevotella intermedia, Bacteroides forsythus, Treponema denticola, Fusobacterium nucleatum, Campylobacter rectus, Eikenella corrodens, Veillonella* spp., *Micromonas micros, Porphyromonas cangingivalis, Haemophilus actinomycetemcomitans Actinomyces* spp., *Bacillus* spp., *Mycobacterium* spp., *Fusobacterium* spp., *Streptococcus* spp., *Staphylococcus aureus, Streptococcus pyogenes, Streptococcus agalectiae, Proteus mirabilis, Klebsiella pneumoniae, Acinetobacter* spp., *Enterococcus* spp., *Prevotella* spp., *Porphyromonas* spp., *Clostridium* spp., *Stenotrophomonas maltophilia, P. cangingivalis, Candida albicans, Escherichia coli* and/or *Pseudomonas aeruginosa*. In certain embodiments, the bacteria are *S. mutans*, which is present within biofilms found in the oral cavity, e.g., on the surface of teeth.

Iron Oxide Nanoparticles (IO-NPs) and IO-NP Compositions

The presently disclosed subject matter provides compositions that include one or more IO-NPs (also referred to herein as catalytic nanoparticles, CAT-NPs and MNPs) for the treatment and/or elimination of biofilms and/or the prevention of biofilm formation. For example, and not by way of limitation, compositions disclosed herein can be used to treat existing biofilms, e.g., biofilms already present on a surface. In certain embodiments, compositions of the present disclosure can be used to prevent the initiation and/or formation of biofilms, e.g., by coating a surface with a disclosed composition.

As disclosed herein, the IO-NPs of the present disclosure can bind to tooth surfaces as well as penetrate and be retained within a biofilm to disrupt the extracellular matrix of the biofilm and reduce the growth and/or kill the bacteria embedded within the biofilm. For example, and not by way of limitation, the IO-NPs of the disclosed subject matter can release iron into the biofilm to reduce the growth of bacteria within the biofilm. In certain embodiments, the IO-NPs release iron in the acidic microenvironments of the biofilm. For example, and not by way of limitation, the IO-NPs can release iron at a pH of about 5.5 or lower, of about 4.5 or lower or of about 4.0 or lower. In certain embodiments, the IO-NPs do not significantly release iron at a pH of about 7.

In certain embodiments, the IO-NPs of the present disclosure can be nanoparticles made from an iron oxide. For example, and not by way of limitation, the IO-NPs can be made from $Fe_3O_4$, $Fe_2O_3$, nanomaterials that contain iron oxides or combinations thereof. In certain embodiments, the IO-NPs can have an iron concentration of about 0.01 to about 10.0 mg/ml. For example, and not by way of limitation, the IO-NPs can have an iron concentration from about 0.01 to about 9.0 mg/ml, from about 0.01 to about 8.0 mg/ml from about 0.01 to about 7.0 mg/ml, from about 0.01 to about 6.0 mg/ml, from about 0.01 to about 5.0 mg/ml, from about 0.01 to about 4.0 mg/ml, from about 0.01 to about 3.0 mg/ml, from about 1.0 to about 2.0 mg/ml, from about 2.0 to about 10.0 mg/ml, from about 3.0 to about 10.0 mg/ml, from about 4.0 to about 10.0 mg/ml, from about 5.0 to about 10.0 mg/ml, from about 6.0 to about 10.0 mg/ml, from about 7.0 to about 10.0 mg/ml, from about 8.0 to about 10.0 mg/ml or from about 9.0 to about 10.0 mg/ml. In certain embodiments, the IO-NPs can have an iron concentration of about 5.0 to about 6.0 mg/ml.

In certain embodiments, the IO-NPs of the present disclosure do not include a polymeric coating. In certain embodiments, the IO-NPs of the present disclosure can include a polymeric coating, for example, and not by way of limitation, the polymeric coating can include chitosan, poly (acrylic acid), dextran, poly(oligo(ethylene glycol) methacrylate-co-methacrylic acid), polyglycidyl methacrylate, poly(vinylalcohol), diols, catechols/dopamines, hydroxamic acids, phosphine oxides, silanes and other coatings known to those familiar in the art. In certain embodiments, the polymeric coating can be dextran or a modified dextran. For example, and not by way of limitation, the dextran can be cross-linked, aminated, carboxylated or modified with diethylaminoethyl moieties. Non-limiting examples of commercially available dextran-coated iron oxide nanoparticles that can be used as the IO-NPs of the present disclosure include Feridex®, Combidex® and Feraheme®. In certain embodiments, the dextran used in the coating of IO-NPs of the present disclosure can have a molecular weight from about 1 kDa to about 100 kDa, e.g., from about 1 kDa to about 90 kDa, from about 1 kDa to about 80 kDa, from about 1 kDa to about 70 kDa, from about 1 kDa to about 60 kDa, from about 1 kDa to about 50 kDa, from about 1 kDa to about 40 kDa, from about 1 kDa to about 30 kDa, from about 1 kDa to about 20 kDa, from about 1 kDa to about 10 kDa, from about 1 kDa to about 5 kDa, from about 5 kDa to about 100 kDa, from about 10 kDa to about 100 kDa, from about 20 kDa to about 100 kDa, from about 30 kDa to about 100 kDa, from about 40 kDa to about 100 kDa, from about 50 kDa to about 100 kDa, from about 60 kDa to about 100 kDa, from about 70 kDa to about 100 kDa, from about 80 kDa to about 100 kDa or from about 90 kDa to about 100 kDa.

In certain embodiments, the IO-NPs of the present disclosure can have a diameter from about 1 nanometer (nm) to about 1000 nm, e.g., as measured by transmission electron microscopy (TEM). For example, and not by way of limitation, the IO-NPs can have a diameter from about 1 nm to about 900 nm, from about 1 nm to about 800 nm, from about 1 nm to about 700 nm, from about 1 nm to about 600 nm, from about 1 nm to about 500 nm, from about 1 nm to about 400 nm, from about 1 nm to about 300 nm, from about 1 nm to about 200 nm, from about 1 nm to about 100 nm, from about 1 nm to about 75 nm, from about 1 nm to about 50 nm, from about 1 nm to about 25 nm, from about 25 nm to about 900 nm, from about 75 nm to about 900 nm, from about 100 nm to about 900 nm, from about 200 nm to about 900 nm, from about 300 nm to about 900 nm, from about 400 nm to about 900 nm, from about 500 nm to about 900 nm, from about 600 nm to about 900 nm, from about 700 nm to about 900 nm or from about 800 nm to about 900 nm. In certain embodiments, the IO-NPs can have a diameter from about 200 nm to about 300 nm. In certain embodiments, the IO-NPs can have a diameter from about 185 nm to about 240 nm, e.g., about 213 nm.

In certain embodiments, the IO-NPs of the present disclosure can have a hydrodynamic diameter from about 1 nm to about 1000 nm. For example, and not by way of limitation, the IO-NPs can have a hydrodynamic diameter from about 10 nm to about 100 nm, from about 15 nm to about 100 nm, from about 20 nm to about 100 nm, from about 25 nm to about 100 nm, from about 30 nm to about 100 nm, from about 35 nm to about 100 nm, from about 40 nm to about 100 nm, from about 45 nm to about 100 nm, from about 50 nm to about 100 nm, from about 55 nm to about 100 nm, from about 60 nm to about 100 nm, from about 65 nm to about 100 nm, from about 70 nm to about 100 nm, from about 75 nm to about 100 nm, from about 80 nm to about 100 nm, from about 85 nm to about 100 nm, from about 90 nm to about 100 nm, from about 95 nm to about 100 nm, from about 5 nm to about 95 nm, from about 5 nm to about 90 nm, from about 5 nm to about 85 nm, from about 5 nm to about 80 nm, from about 5 nm to about 75 nm, from about 5 nm to about 70 nm, from about 5 nm to about 65 nm, from about 5 nm to about 60 nm, from about 5 nm to about 55 nm, from about 5 nm to about 50 nm, from about 5 nm to about 45 nm, from about 5 nm to about 40 nm, from about 5 nm to about 35 nm, from about 5 nm to about 30 nm, from about 5 nm to about 25 nm, from about 5 nm to about 20 nm, from about 5 nm to about 15 nm or from about 5 nm to about 10 nm. In certain embodiments, the IO-NPs can have a hydrodynamic diameter from about 30 nm to about 50 nm.

In certain embodiments, an IO-NP, e.g., the core of an IO-NP, of the present disclosure can be doped with a metal, e.g., as a metal salt. For example, and not by way of limitation, the metal can be manganese (Mn), cobalt (Co), nickel (Ni), magnesium (Mg), strontium (Sr), barium (Ba), scandium (Sc), titanium (Ti), vanadium (V), chromium (Cr), copper (Cu), zinc (Zn), aluminum (Al), yttrium (Y), zirconium (Zr), niobium (Nb), molybdenum (Mo), ruthenium (Ru), rhodium (Rh), palladium (Pd), hafnium (Hf), tantalum (Ta), Tungsten (W), rhenium (Re), osmium (Os), iridium (Ir), platinum (Pt), copper (Cu) or a combination thereof. In certain embodiments, the metals can be present as a salt such as, but not limited to, $MnCl_2$, $CoCl_2$, $NiCl_2$ and $MgCl_2$. In certain embodiments, IO-NPs of the present disclosure can be doped with an alkaline earth metal such as, but not limited to, calcium (Ca), e.g., as calcium phosphate. In certain embodiments, the doping metal can be present in the IO-NPs (e.g., within the core of the IO-NPs) at about 1% to about 50% by weight, e.g., from about 1% to about 40%, from about 1% to about 30%, from about 1% to about 20%, from about 1% to about 10%, from about 1% to about 5%, from about 5% to about 50%, from about 10% to about 50%, from about 20% to about 50%, from about 30% to about 50% or from about 40% to about 50% by weight. In certain embodiments, the IO-NPs doped with a metal can have a doping metal concentration of about 0.01 to about 10.0 mg/ml, e.g., from about 0.01 to about 9.0 mg/ml, from about 0.01 to about 8.0 mg/ml from about 0.01 to about 7.0 mg/ml, from about 0.01 to about 6.0 mg/ml, from about 0.01 to about 5.0 mg/ml, from about 0.01 to about 4.0 mg/ml, from about 0.01 to about 3.0 mg/ml, from about 1.0 to about 2.0 mg/ml, from about 2.0 to about 10.0 mg/ml, from about 3.0 to about 10.0 mg/ml, from about 4.0 to about 10.0 mg/ml, from about 5.0 to about 10.0 mg/ml, from about 6.0 to about 10.0 mg/ml, from about 7.0 to about 10.0 mg/ml, from about 8.0 to about 10.0 mg/ml or from about 9.0 to about 10.0 mg/ml. In certain embodiments, the IO-NPs doped with a metal can have a doping metal concentration of about 5.0 to about 6.0 mg/ml.

In certain embodiments, an IO-NP of the present disclosure can be conjugated to one or more matrix degrading and/or peroxide producing enzymes. For example, and not by way of limitation, the enzyme conjugated to the IO-NP can degrade components within the biofilm matrix, e.g., glucans and fructans, to generate glucose and fructose, and release $H_2O_2$ into the biofilm. IO-NPs can then catalyze the $H_2O_2$ to generate free radicals for matrix degradation and/or bacteria killing. Furthermore, the matrix degrading enzymes can help to degrade the biofilm matrix. Non-limiting examples of suitable enzymes include dextranase, mutanase, glucose/fructose/galactose-oxidase and combinations thereof. Additional non-limiting examples of matrix-degrading enzymes include DNAse, nucleases, dispersin, glycosyde hydrolases, proteases, subtilisins and glucanohydrolases. The enzymes can be conjugated to the IO-NP using any technique known in the art. In certain embodiments, an enzyme can be conjugated to the IO-NP using electrostatic attachment of the IO-NP to the charged groups of the enzyme. Alternatively or additionally, an enzyme can be conjugated to a polymer coated IO-NP using glutaraldehyde or carbodiimide/N-hydroxysuccinimide to activate the IO-NP followed by crosslinking the activated IO-NP to amine groups of the enzyme.

The present disclosure further provides compositions that include one or more IO-NPs described herein, e.g., an IO-NP and/or an IO-NP conjugated to an enzyme, and $H_2O_2$. In certain embodiments, the IO-NPs present within the composition have a polymeric coating, e.g., dextran. In certain embodiments, the IO-NPs present within the composition do not have polymeric coating. In certain embodiments, the $H_2O_2$ present in the composition could be generated from other chemicals like sodium percarbonate. For example, and not by way of limitation, a composition of the present disclosure can include sodium percarbonate, which in turn, generates $H_2O_2$.

In certain embodiments, the composition can include $H_2O_2$ at a concentration of about 0.01% to about 3.0% v/v. In certain embodiments, the composition can include $H_2O_2$ at a concentration of about 0.05% to about 3.0%, 5%, of 0.1% to about 0.25%, of about 0.1% to about 0.5%, of about 0.1% to about 0.75%, of about 0.1% to about 1.0%, of about 0.1% to about 1.5%, of about 0.1% to about 1.75%, of about 0.1% to about 2.0%, of about 0.1% to about 2.25%, of about 0.1% to about 2.5% or of about 0.1% to about 2.75%. In certain embodiments, the one or more IO-NPs catalyze $H_2O_2$ to form one or more free radicals that can degrade and/or digest the extracellular matrix of the biofilm and/or kill bacteria. For example, and not by way of limitation, the one or more free radicals can degrade the extracellular matrix of the biofilm and kill bacteria simultaneously. In certain embodiments, the IO-NPs can catalyze $H_2O_2$ to produce free radicals, for example, and not by way of limitation, hydroxyl radicals (.OH).

In certain embodiments, a composition of the present disclosure can include IO-NPs that vary in size (e.g., diameter) and composition. For example, and not by way of limitation, a composition of the present disclosure can include a mixture of IO-NPs that have a polymeric coating and IO-NPs that do not have a polymeric coating. In certain embodiments, a composition of the present disclosure can include a mixture of IO-NPs that have different polymeric coatings, e.g., one or more IO-NPs within the composition can have a dextran coating and one or more IO-NPs within the composition can have a modified dextran coating. Alternatively or additionally, in certain embodiments, a composition of the present disclosure can include IO-NPs that vary in composition, e.g., a composition of the present disclosure can include a mixture of IO-NPs that were doped with different metals, e.g., Mg and/or Mn.

Formulations and Products

The presently disclosed subject matter further provides formulations that incorporate the disclosed IO-NP compositions, e.g., a composition that includes one or more IO-NPs and/or a composition that includes one or more IO-NPs and $H_2O_2$. For example, and not by way of limitation, the formulations can include oral care products and products for delivering the composition into the oral cavity and commercial products for the delivery of the composition into a medical device, a naval material and/or vessel or industrial material. In certain embodiments, the compositions can be incorporated in materials for use in manufacturing medical devices, e.g., medical tubing and catheters, for use in manufacturing oral prosthetics, e.g., dentures and implants, and for use in manufacturing industrial materials, e.g., pipes or ship hulls. In certain embodiments, formulations of the present disclosure can be applied topically, e.g., applied to chronic wounds or skin diseases as treatment. In certain embodiments, formulations of the present disclosure can be used as a spray and/or paint to coat one or more surfaces of an industrial material or a ship hull.

In certain embodiments, a composition and/or formulation of the present disclosure can include IO-NPs, as disclosed above, at a concentration from about 0.01 mg/ml to about 5 mg/ml, e.g., from about 0.01 mg/ml to about 4 mg/ml, from about 0.01 mg/ml to about 3 mg/ml, from about 0.01 mg/ml to about 2 mg/ml, from about 0.01 mg/ml to about 1 mg/ml, from about 0.01 mg/ml to about 0.75 mg/ml, from about 0.01 mg/ml to about 0.5 mg/ml, from about 0.01 mg/ml to about 0.1 mg/ml, from about 0.01 mg/ml to about 0.05 mg/ml, from about 0.05 mg/ml to about 5 mg/ml, from about 0.1 mg/ml to about 5 mg/ml, from about 0.5 mg/ml to about 5 mg/ml, from about 1 mg/ml to about 5 mg/ml, from about 2 mg/ml to about 5 mg/ml, from about 3 mg/ml to about 5 mg/ml or from about 4 mg/ml to about 5 mg/ml. In certain embodiments, a formulation and/or composition of the present disclosure can include IO-NPs at a concentration of about 0.5 mg/ml.

In certain embodiments, a formulation of the present disclosure can include a composition as disclosed above and fluoride, e.g., as sodium fluoride. In certain embodiments, fluoride can be present within a formulation of the present disclosure at a concentration of about 10 parts per million (ppm) to about 5,000 ppm, e.g., from about 100 ppm to about 4,500 ppm, from about 100 ppm to about 4,000 ppm, from about 100 ppm to about 3,500 ppm, from about 100 ppm to about 3,000 ppm, from about 100 ppm to about 2,500 ppm, from about 100 ppm to about 2,000 ppm, from about 100 ppm to about 1,500 ppm, from about 100 ppm to about 1,000 ppm, from about 100 ppm to about 500 ppm or from about 200 ppm to about 400 ppm. In certain embodiments, fluoride is present at a concentration from about 200 ppm to about 300 ppm, e.g., about 250 ppm. In certain embodiments, fluoride is present at a concentration of about 5,000 ppm.

In certain embodiments, the IO-NP compositions of the present disclosure, e.g., a composition that includes one or more IO-NPs conjugated to an enzyme, can be incorporated into a formulation for delivering the composition into the oral cavity. For example, and not by way of limitation, the composition can be incorporated into a liquid or gel formulation, spray. In certain embodiments, the liquid formulation can include a carrier such as, but not limited to, saline, dextrose, water, isotonic saline, oils, e.g., vegetable oils or mineral oils, oily esters and alcohols, e.g., ethyl alcohol. In certain embodiments, the liquid formulation can further include one or more additional components including suspending agents, dispersing or wetting agents, emulsifying agents, demulcents, preservatives, buffers, salts, flavorings, coloring agents, sweetening agents and thickening agents. In certain embodiments, the IO-NP compositions of the present disclosure can be incorporated into an oral care product. Non-limiting examples of oral care products include toothpastes, mouth rinses, teeth whitening products, abrasive dentifrice gels, denture washes, nonabrasive dentifrice gels, denture washes or soaks, denture adhesives or cements, gels, emulsions, varnishes, restorative materials (e.g., ceramic, resin, etc.), dental filling materials, oral gel-strip products, chewing gums, candies and beverages. The formulations intended for oral use can be prepared according to any method known in the art.

In certain embodiments, the IO-NP compositions of the present disclosure can be incorporated into a formulation for the delivery of the composition into a medical device or industrial material. For example, the composition can be incorporated into a liquid formulation as disclosed above. In certain embodiments, the composition can be incorporated into a lubricant, ointment, cream or gel that includes a diluent (e.g., Tris, citrate, acetate or phosphate buffers) having various pH values and ionic strengths, solubilizer such as TWEEN™ or Polysorbate, preservatives such as thimerosal, parabens, benzylalconium chloride or benzyl alcohol, antioxidants such as ascorbic acid or sodium metabisulfite and other components such as lysine or glycine. Alternatively or additionally, catheter or medical tubing materials can be impregnated with an IO-NP composition of the present disclosure for preventing the formation of biofilms on the surface of and/or within the catheter or tubing.

Methods of Use

The presently disclosed subject matter further provides methods for using the disclosed compositions and/or formulations. The methods of the present disclosure can be used to treat and/or prevent biofilms and/or biofilm-related infections. For example, and not by way of limitation, administration of a composition or formulation of the present disclosure can be used to inhibit the formation of biofilms, inhibit further accumulation of biofilm, promote the disruption or disassembly of existing biofilms and/or weaken an existing biofilm. For example, but not by way of limitation, the compositions and/or formulations of the present disclosure can be used to treat biofilms that promote oral disease. Oral diseases can include, but are not limited to, diseases and disorders that affect the oral cavity or associated medical conditions. For example, oral diseases include, but are not limited to, dental caries, as well as periodontal diseases such as gingivitis, adult periodontitis, early-onset periodontitis, peri-implantitis and endodontic infections.

In certain embodiments, a composition or formulation of the present disclosure can be used to treat and/or prevent biofilm-associated mucosal infections including, for example, denture stomatitis and oral candidiasis. In certain embodiments, methods of the disclosed subject matter can be used to treat and/or prevent diseases or disorders, e.g., biofilm-associated diseases, including, but not limited to, dental caries, mucosal infections, oral diseases, urinary tract infections, catheter infections, middle-ear infections, wounds, infections of implanted medical devices, e.g., artificial joints and artificial valves, and human infections.

As used herein, "treatment" (and grammatical variations thereof such as "treat" or "treating") refers to clinical intervention in an attempt to alter the natural course of the individual being treated, and can be performed either for prophylaxis or during the course of the disease. Desirable effects of treatment include, but are not limited to, preventing occurrence or recurrence of the disease, alleviation of symptoms, diminishment of any direct or indirect pathological consequences of the disease, decreasing the rate of disease progression or amelioration of the disease state. In certain embodiments, the compositions and formulations of the present disclosure can be used to delay development of a disease or to slow the progression of a disease. In certain embodiments, treatment can refer to the elimination, removal and/or reduction of existing biofilms. In certain embodiments, prevention can refer to impeding the initiation or formation of a biofilm on a surface.

An "individual," "patient" or "subject," as used interchangeably herein, refers to a mammal. Mammals include, but are not limited to, domesticated animals (e.g., cows, sheep, cats, dogs and horses), primates (e.g., humans and non-human primates such as monkeys), rabbits and rodents (e.g., mice and rats). In certain embodiments, the individual or subject is a human.

In certain embodiments, methods for the prevention and treatment of an oral disease and/or for the prevention and treatment of biofilms in a subject can include administering an effective amount of a composition and/or formulation of the present disclosure to a subject. In certain embodiments, the method includes administering to a subject a composition or formulation that includes an IO-NP and/or an IO-NP conjugated to an enzyme. In certain embodiments, a composition and/or formulation of the present disclosure can be administered to the subject for a short time interval such as, but not limited to, a time period of less than about 10 minutes, less than about 9 minutes, less than about 8 minutes, less than about 7 minutes, less than about 6 minutes, less than about 5 minutes, less than about 4 minutes less, than about 3 minutes, less than about 2 minutes or less than about 1 minute.

An "effective amount," as used herein, refers to an amount effective, at dosages and for periods of time necessary, to achieve the desired therapeutic or prophylactic result. For the prevention or treatment of disease, the appropriate amount, e.g., effective amount, of a composition or formulation of the present disclosure will depend on the type of disease to be treated or prevented and the severity and course of the disease. Dosage regimens may be adjusted to provide the optimum therapeutic response.

In certain embodiments, the method can further include the administration of hydrogen peroxide, e.g., by the administration of a solution that includes hydrogen peroxide, to the subject. Alternatively or additionally, hydrogen peroxide can be present in the composition and/or formulation that includes the IO-NPs. For example, and not by way of limitation, hydrogen peroxide can be formulated in a gel-like product, e.g., toothpaste, using sodium percarbonate, where the gel-like product further includes one or more IO-NPs. In certain embodiments, sodium percarbonate can be present within the composition and/or formulation to release hydrogen peroxide in the presence of water or when placed in the mouth. Such compositions and/or formulations can allow the release of hydrogen peroxide from the composition and/or formulation when contacted with an aqueous solution or when placed in the mouth, thereby allowing the reaction between the hydrogen peroxide and the IO-NPs to occur in situ.

In certain embodiments, the solution, composition and/or formulation can include hydrogen peroxide at a concentration of about 0.1% to about 0.25%, of about 0.1% to about 0.5%, of about 0.1% to about 0.75%, of about 0.1% to about 1.0%, of about 0.1% to about 1.5%, of about 0.1% to about 1.75%, of about 0.1% to about 2.0%, of about 0.1% to about 2.25%, of about 0.1% to about 2.5%, of about 0.1% to about 2.75% or of about 0.1% to about 3.0%. In certain embodiments, the solution, composition and/or formulation can include hydrogen peroxide at a concentration of about 0.1% to about 1.0%. In certain embodiments, the solution, composition and/or formulation can include hydrogen peroxide at a concentration of about 0.1% to about 0.5%.

In certain embodiments, the method can further include the administration of an effective amount of fluoride. In certain embodiments, fluoride can be present in the composition and/or formulation that includes the IO-NPs and/or hydrogen peroxide. For example, and not by way of limitation, fluoride can be formulated in a gel-like product, as disclosed above, where the gel-like product further includes one or more IO-NPs and/or hydrogen peroxide. In certain embodiments, fluoride can be present within a composition and/or formulation of the present disclosure at a concentration of about 10 parts per million (ppm) to about 10,000 ppm, e.g., about 5,000 ppm.

In certain embodiments, a composition or formulation of the present disclosure can be administered to the subject one time or over a series of treatments. In certain embodiments, several divided doses may be administered daily or the dose may be proportionally reduced as indicated by the exigencies of the therapeutic situation. For example, but not by way of limitation, the compositions and formulations disclosed herein can be administered to a subject twice every day, once every day, once every two days, once every three days, once every four days, once every five days, once every six days, once a week, once every two weeks, once every three weeks, once every month, once every two months, once every three months, once every six months or once every year. In certain embodiments, a composition or formulation of the present disclosure, e.g., a composition that includes one or more IO-NPs and/or one or more IO-NPs conjugated to a matrix degrading and/or peroxide producing enzyme, can be administered to a subject twice every day. In certain embodiments, a composition that includes one or more IO-NPs, e.g., in a mouth rinse formulation, can be administered to a subject once or twice every day, followed by the administration of $H_2O_2$ once or twice every day, once every two days, once every three days, once every four days, once every five days, once every six days or once a week. In certain embodiments, a composition that includes one or more IO-NPs and sodium percarbonate, which in turn, generates $H_2O_2$, can be administered to a subject, e.g., in a gel-based formulation, once or twice every day, once every two days, once every three days, once every four days, once every five days, once every six days or once a week.

The present disclosure further provides methods for the prevention of bacterial growth in a biofilm. In certain embodiments, such methods can include contacting a surface having a biofilm with an effective amount of a composition and/or formulation, disclosed herein, that includes one or more iron nanoparticles. In certain embodiments, the one or more iron nanoparticles bind to the surface and releases iron to inhibit bacterial growth within the biofilm.

The present disclosure further provides methods for preventing the formation of a biofilm on a surface. In certain embodiments, a method for preventing the formation of a biofilm on a surface can include treating a surface that is "at risk" for biofilm development with an effective amount of a composition and/or formulation, disclosed herein, that includes one or more iron nanoparticles. In certain embodiments, the method can further include contacting the "at risk" surface with $H_2O_2$. For example, and not by way of limitation, an effective amount of a composition and/or formulation, disclosed herein, that includes one or more iron nanoparticles, can be coated on the surface, e.g., by spraying or painting. Surfaces that are "at risk" for developing a biofilm include, but are not limited to, apatitic surfaces, e.g., bone and tooth surfaces, endodontic canals, implant surfaces, medical device surfaces, e.g., catheters and instruments, and industrial and naval surfaces, e.g., pipe and ship hull surfaces. In certain embodiments, the surface can be the interior and/or exterior surface of a medical device and industrial and/or naval material.

The presently disclosed subject matter further provides methods for preventing tooth demineralization. In certain embodiments, a method for the prevention of demineralization can include contacting a tooth-enamel or an apatitic (e.g., bone) surface having a biofilm with an effective amount of a composition that includes one or more iron nanoparticles. In certain embodiments, the one or more iron nanoparticles bind to the surface to inhibit and/or prevent enamel or apatitic dissolution.

The presently disclosed subject matter further provides methods for the treatment and elimination of biofilms and/or the prevention of biofilm formation on a surface of a medical device or an industrial and/or naval material. In certain embodiments, the method can include contacting a medical device, e.g., catheters, implants, artificial joints, tubing, any implanted devices, or an industrial and/or naval material, e.g., a pipe, containers, reactors, turbines or ship hulls with a composition or formulation disclosed herein. In certain embodiments, the method can include contacting a surface of a medical device or industrial material with a composition or formulation that includes an IO-NP or an IO-NP conjugated to an enzyme. In certain embodiments, the method can further include contacting the surface of a medical device or industrial material with $H_2O_2$. In certain embodiments, a composition or formulation of the present disclosure can be incorporated into a material for manufacturing a medical device or an industrial and/or naval material to prevent, minimize and/or reduce the formation of a biofilm on a surface of the medical device or industrial and/or naval material.

Kits

The presently disclosed subject matter further provides kits for the treatment and/or prevention of biofilms as described above. For example, and not by way of limitation, a kit of the present disclosure can include one or more compositions or formulations disclosed herein, e.g., in one or more containers.

In certain embodiments, the kit can include a container that includes one or more compositions or formulations described herein and a label or package insert on or associated with the container. In certain embodiments, a kit of the presently disclosed subject matter can include a container that includes an IO-NP composition or formulation of the presently disclosed subject matter. In certain embodiments, a kit of the presently disclosed subject matter can include a first container that includes an IO-NP composition or formulation of the presently disclosed subject matter and a second container that includes hydrogen peroxide. In certain embodiments, the kit can further include instructions for use, such as a dosing regimen. Non-limiting examples of suitable containers include bottles, vials, solution bags and the like. The containers can be formed from a variety of materials such as glass or plastic.

The following example is offered to more fully illustrate the invention, but is not to be construed as limiting the scope thereof.

Example 1

Biofilms develop as microbes accumulate on surfaces, forming structured communities encapsulated within an extracellular matrix that includes polymeric substances such as exopolysaccharides (EPS). The extracellular matrix creates spatial and microenvironmental heterogeneity and provides a diffusion-limiting barrier in biofilms, thereby modulating the growth and protection of pathogens against antimicrobials locally. Therefore, matrix essentially hinders drug efficacy to treat biofilms and biofilm-associated maladies.

Within the complex oral microbiome, *Streptococcus mutans* (*S. mutans*) is not always the most abundant organism. However, *S. mutans* can rapidly orchestrate the formation of cariogenic biofilms on pellicle-coated teeth when frequently exposed to sucrose via EPS synthesis on the pellicle and on bacterial surfaces. EPS formed in situ promote local accumulation of microbes on teeth while forming a spatially heterogeneous and diffusion-limiting matrix. In parallel, sugars are fermented by bacteria embedded in the matrix, which create highly acidic microenvironments (FIG. 1). The low pH niches induce EPS synthesis while cariogenic (acid-tolerant and acidogenic) flora prosper. Consequently, local acidity ensures continuous biofilm accretion and acid-dissolution of adjacent tooth enamel, leading to the onset of dental caries. In addition, local bacterial clusters, delineated by the extracellular matrix, become recalcitrant to antimicrobials, making biofilm elimination extremely difficult. These processes are representative to other biofilms and related infections as the matrix creates protective and disease-causing environments while hindering drug efficacy.

To be effective in eliminating the biofilm and the microorganisms, e.g., microbes enmeshed within EPS extracellular matrix, anti-biofilm agents would need to be retained locally and disrupt the matrix assembly, degrade existing matrix and/or target embedded bacteria within an acidic environment. At the same time, acid-dissolution of enamel should be blocked locally. This Example discloses an anti-biofilm agent that includes iron oxide nanoparticles (IO-NPs; also referred to herein as MNPs and CAT-NPs), which have biomimetic properties such as peroxidase-like activity (Gao et al., Nature Nanotech, 2007), to eliminate pathogenic oral biofilms. IO-NPs have received increased attention in many fields of biomedicine and green chemistry because of its nanocatalytic properties, bioactivity and safety. Furthermore, IO-NPs are economical (low-cost and easy to produce) and environmentally safe (Hudson et al., Green Chemistry, 2014), and are also one of the earliest nanomaterials to receive FDA-approval for clinical application.

Figures 2A, 2B, 2C:
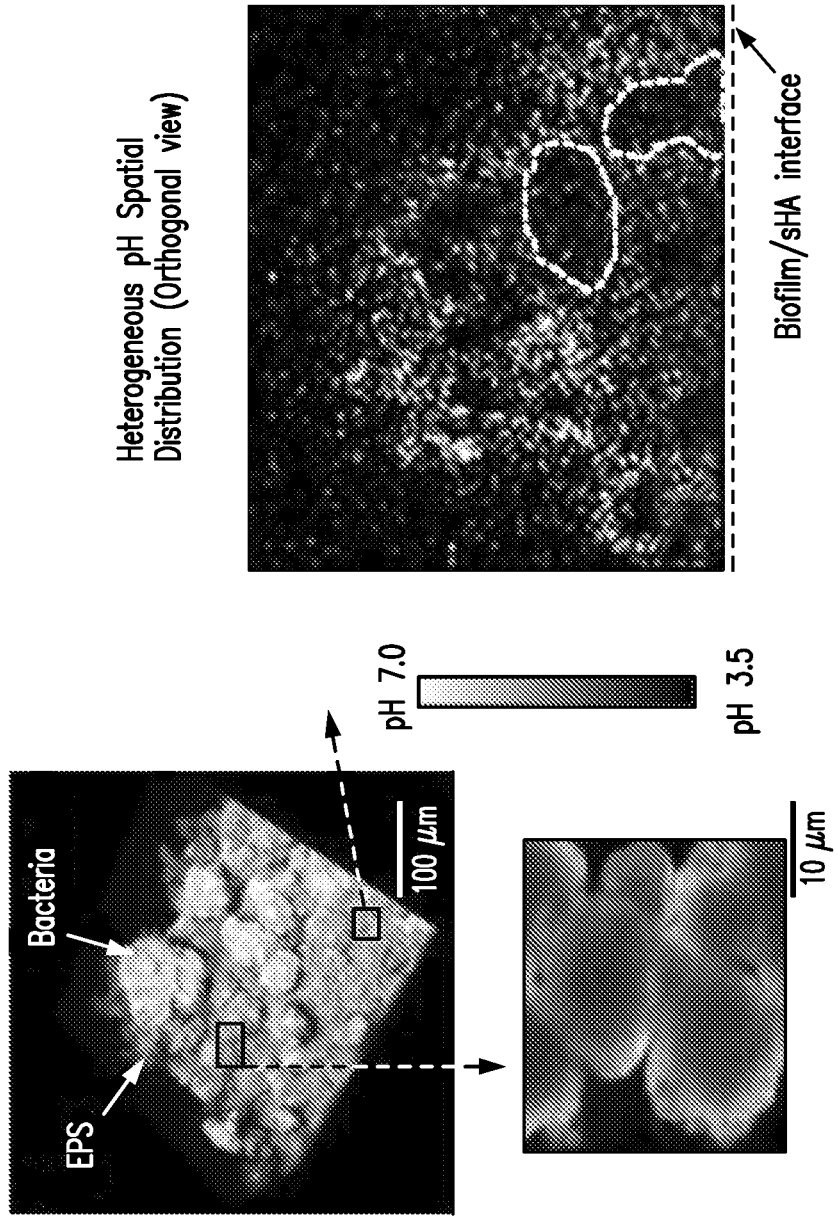
FIGS. 2A-2C depict images of a three dimensional (3D) extracellular matrix and acidic pH niches within a biofilm.

The anti-biofilm composition of this Example uses a biocompatible IO-NP with biomimetic (catalytic) and pH responsive properties that synergizes with $H_2O_2$ to effectively disrupt cariogenic biofilms, and provides an exciting and innovative approach for biofilm elimination using IO-NP in combination with $H_2O_2$ that is capable of breaking down the EPS extracellular matrix and effectively killing bacteria within the biofilm at low pH (FIG. 1 and FIG. 2).

Figure 3:
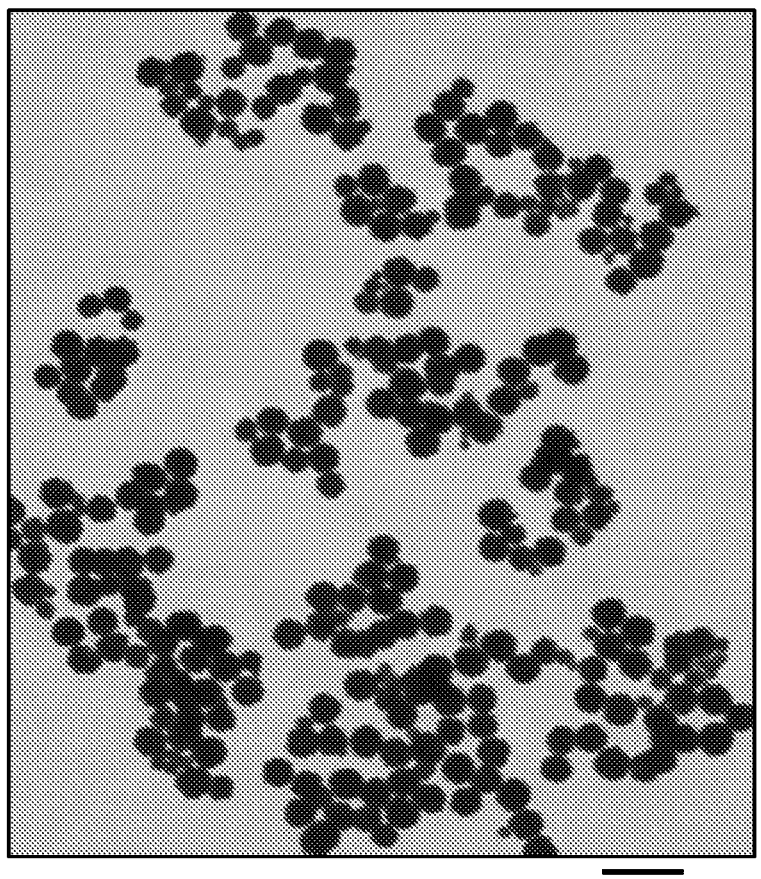
FIG. 3 depicts a TEM image of IO-NPs prepared and characterized according to non-limiting embodiments of the present disclosure. Scale bar is 500 nm.

IO-NPs can be synthesized using readily available materials via a simple and suitable approach, which can be scaled up at very low cost. IO-NPs were generated by a hydrothermal method as previously described (Gao et al., Nanoscale, 2014). Briefly, ferric chloride ($FeCl_3$) and sodium acetate can be mixed into ethylene glycol in an autoclave reactor and incubated at 200° C. for certain time. The generated IO-NPs are then collected for further application. FIG. 3 shows IO-NPs produced by the method disclosed above as visualized under a transmission electron microscope (TEM).

To test the efficacy of the IO-NPs in combination with $H_2O_2$, mature biofilms were formed on saliva-coated hydroxyapatite (sHA) surfaces (a tooth enamel-like material) using S. mutans, a well-established biofilm-forming, acidogenic and matrix-producing oral pathogen. Topical applications of IO-NPs in combination with low doses of $H_2O_2$ (≤0.5%) with a low pH (4.5-6.5) at brief exposures (1 or 5 min) twice-daily were performed to simulate a potential clinical treatment regimen. IO-NPs were able to bind effectively to sHA and were retained within biofilms despite brief topical exposure (FIG. 4).

Figure 5B:
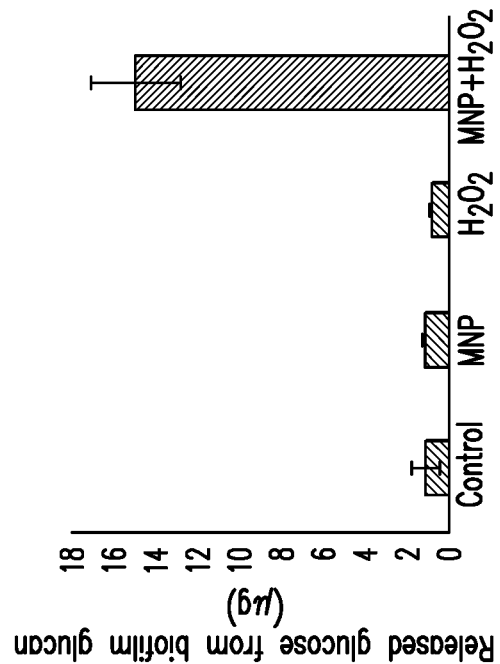
FIGS. 5A-5B depict graphs of bacteria killing and matrix degradation by IO-NPs in combination with 0.5% $H_2O_2$.
Figure 5A:
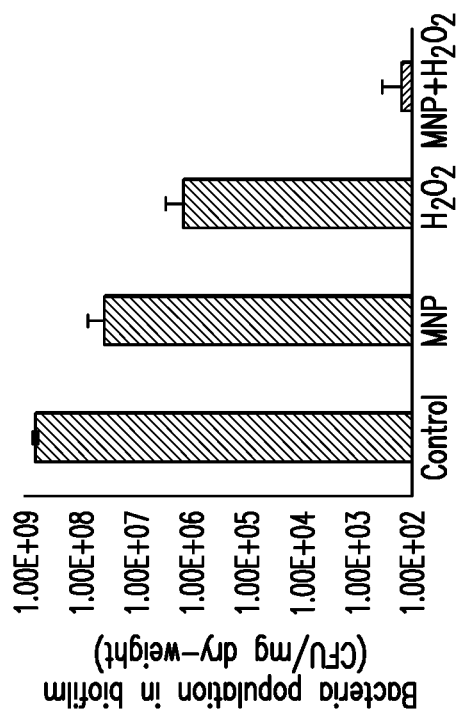

As shown in FIG. 5A, topical applications of IO-NPs in combination with $H_2O_2$ exhibited exceptional killing of S. mutans embedded in the biofilm (>6-log reduction) versus control and >4-log reduction versus $H_2O_2$ alone, eliminating almost entirely the viable bacterial population. In addition, IO-NPs in combination with $H_2O_2$ can also dramatically increase the degradation of extracellular glucans, the main EPS component in the cariogenic biofilm matrix (FIG. 5B), which can effectively disrupt the structural integrity of the biofilm (Xiao et al., PLoS Pathog, 2012). These data demonstrate the potential of IO-NPs to dramatically enhance the anti-microbial efficacy and anti-biofilm activity of $H_2O_2$, a cheap and readily available "green chemical" that is widely used in many clinical applications.

Figure 6A:
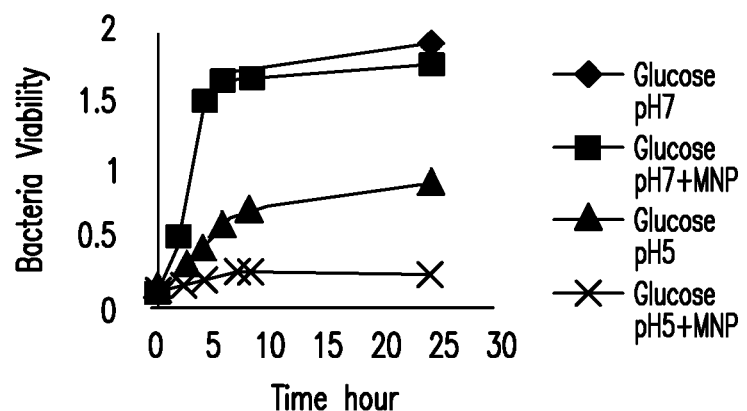
FIGS. 6A-6C depict graphs of bacteria inhibition, iron release from IO-NPs and free radical generation under low pH.
Figure 6B:
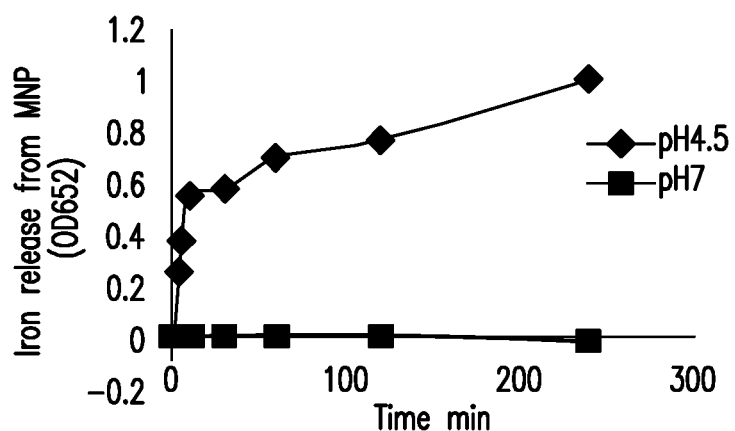
Figure 6C:
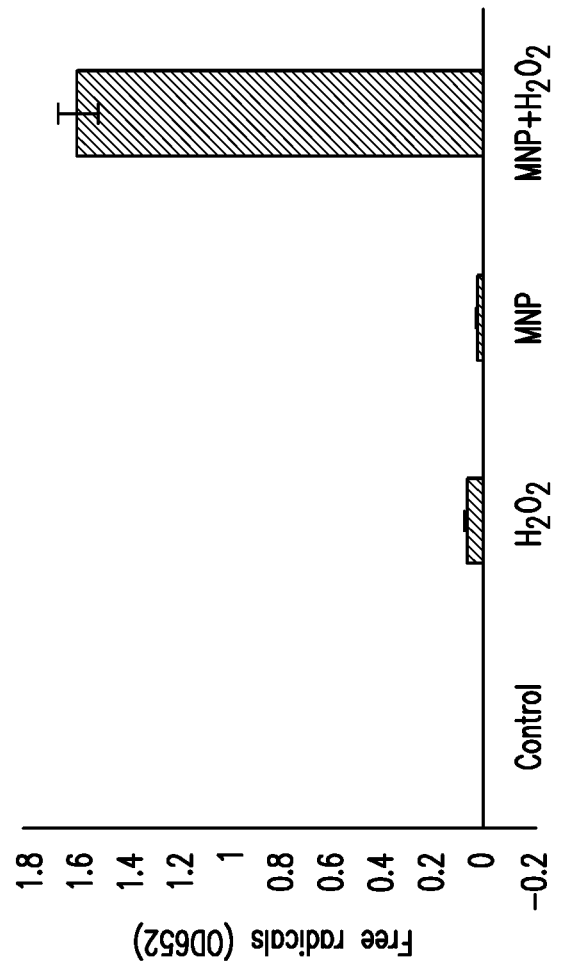
Figure 8A:
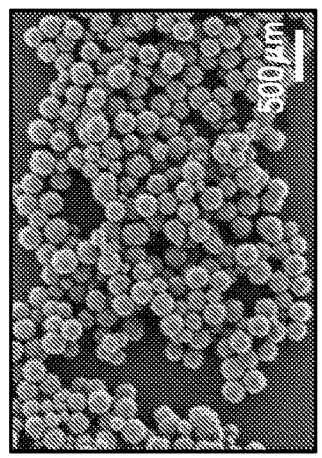
FIGS. 8A-8E depict CAT-NP characterization and catalytic activity.
Figure 8B:
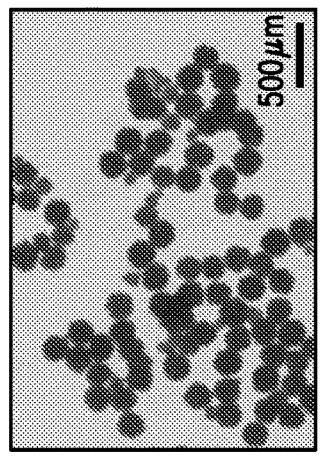
Figure 8C:
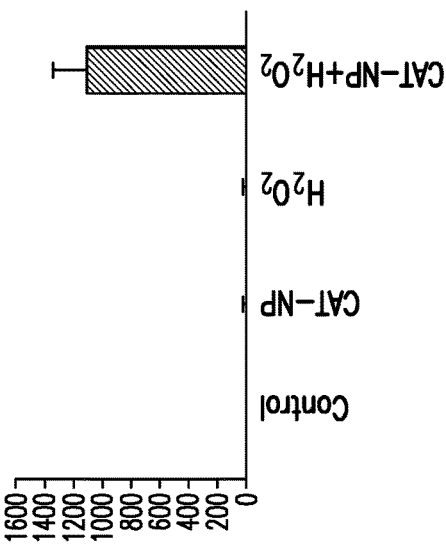
Figure 8D:
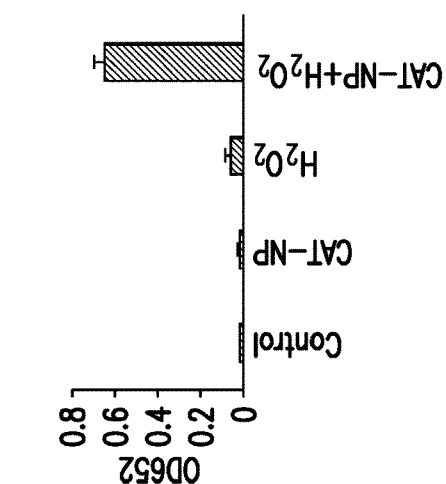
Figure 8E:
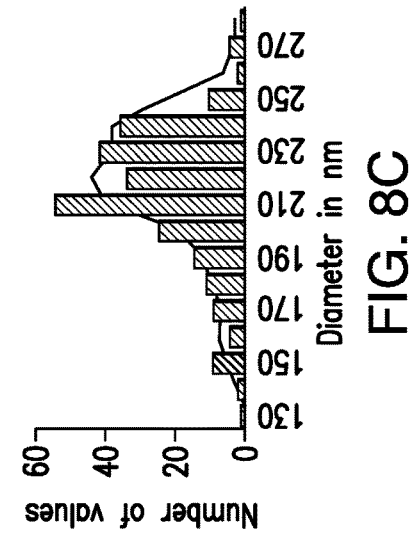

In addition to being effective at low pH, IO-NPs also have the capability to inhibit bacterial viability in culture medium at low pH. As shown in FIG. 6A, S. mutans growth was clearly inhibited at acidic pH (pH 5) using IO-NPs compared to bacterial growth at neutral pH. Furthermore, iron was released from IO-NPs at low pH (pH 4.5) at a physiological temperature (37° C.) (FIG. 6B), which can explain the mechanism of IO-NP inhibition on bacterial growth at acidic pH. Furthermore, and as shown in FIG. 6C, IO-NP catalyzes $H_2O_2$ to dramatically increase the generation of free radicals (FIG. 6C). These data provide evidence that IO-NPs in combination with $H_2O_2$ can produce free radicals under acidic microenvironments found in pathogenic oral biofilms.

As shown in FIG. 7, IO-NPs can also simultaneously block acid dissolution of hydroxyapatite (HA) beads. HA beads were almost completely dissolved after incubation in acidic buffer as compared to untreated HA beads (FIG. 7A-B). In sharp contrast, acid dissolution of HA beads was greatly impaired in the presence of IO-NPs, which shows the potential of using the disclosed anti-biofilm composition for preventing tooth-enamel demineralization (FIG. 7C). These data show that the disclosed anti-biofilm composition could be an ideal anti-biofilm/anti-caries treatment approach. It integrates a comprehensive multifunctional strategy that facilitates matrix disruption and has anti-bacterial action within biofilms, while preventing demineralization under acidic microenvironments. Without being bound to a particular theory, the anti-biofilm agent includes five biological features: (1) IO-NPs (i.e., MNPs) effectively binds to tooth-pellicle, which is a surface at risk for biofilm formation, and is retained within biofilms even after brief topical exposure; (2) IO-NPs are pH responsive, releasing iron at acidic pH that inhibits bacterial growth; (3) IO-NPs catalyze $H_2O_2$ to produce free radicals that efficiently degrade matrix components; (4) IO-NPs can rapidly kill bacteria embedded within biofilms; and (5) prevents apatitic demineralization (FIG. 1).

The disclosed IO-NPs-$H_2O_2$ approach can provide an exceptionally effective strategy for biofilm elimination. IO-NPs can be more advantageous and efficacious than current chemical modalities to control pathogenic oral biofilms. First, IO-NPs can be bound and retained within biofilms even after brief topical exposure. Second, IO-NPs can quickly catalyze low dosages of $H_2O_2$ (0.1-0.5%) to generate free radicals that potentiate disruption of biofilm matrix and killing efficacy of embedded bacteria, and can effectively reduce the amount of $H_2O_2$ typically used in the clinical treatment (up to 10%). Third, it is a pH responsive process in which IO-NP-initiated bioactivity is particularly effective under acidic conditions, precisely when most needed. Fourth, it can reduce acid dissolution of hydroxyapatite, which is critical for prevention of tooth-enamel and bone demineralization. Furthermore, IO-NPs could enhance stain removal from tooth surfaces due to $H_2O_2$ catalysis in situ. As IO-NPs and $H_2O_2$ are FDA-approved and sustainable materials that can be easily synthesized at large scale with very low cost, IO-NPs can be incorporated in a variety of oral care products, including toothpaste or mouthwash. The use of IO-NPs-$H_2O_2$ also has broad applicability as the extracellular matrix and resistance of microbial killing is inherent to most, if not all, biofilms associated with other human diseases as well as industry-related issues.

Example 2

Due to the ease of access to the mouth, oral biofilms serve as an excellent model to explore new concepts for biofilm control. Pathogenic biofilms formed on teeth are examples of how virulent species, such as S. mutans, accumulate and persist on surfaces throughout the development of an EPS-rich matrix (Koo et al., J Dent Res, 2013). The pathogens embedded in the matrix produce highly acidic microenvironments with pH values close to 4.5, which result in acid-dissolution of the enamel-apatite and can lead to the onset and progression of the tooth-decay process, a disease known as dental caries (Koo et al., *J Dent Res*, 2013; Fejerskov et al., *J Dent Res*, 1992). By using experimental models that mimic these pathological conditions, this Example demonstrates the anti-biofilm mechanisms of catalytic nanoparticles (CAT-NP) and the effectiveness of CAT-NPs to activate $H_2O_2$. This Example further shows the effectiveness of CAT-NPs, in combination with $H_2O_2$, to prevent the development of a biofilm-associated oral disease.

Effective retention of iron nanoparticles within biofilms and the in situ activity of iron nanoparticles can play a role in the biological efficacy of the iron nanoparticles in vivo (Hannig and Hannig, *Nature Nanotechnol*, 2010; Allaker and Memarzadeh, *Int J. Antimicrob Agents*, 2014). To examine whether CAT-NPs are retained within biofilms following topical treatment with short-term exposures (5 or 10 min), the following experiments were performed. CAT-NPs were synthesized by the solvothermal method as described below (see, also, Gao et al., *Nat Nanotechnol*, 2007; Deng et al., *Angew Chem Int Edit*, 2005). This method produced nanoparticles having a diameter of 213±26 nm and intrinsic peroxidase-like activity (FIG. 8). Briefly, 0.82 g of $FeCl_3$ was dissolved in 40 ml of ethylene glycol to form a clear solution. Then, 3.6 g of NaAc was added to the solution with vigorous stirring for 30 min. The mixture was then transferred to a 50 ml teflon-lined stainless-steel autoclave and incubated at 200° C. for 12 h. After cooling to room temperature, the precipitate was collected, rinsed several times with ethanol and then dried at 60° C. for 3 h. The synthesized nanoparticles were characterized using scanning electron microscopy (SEM; Philips XL-30 field, 15 kV) and transmission electron microscopy (TEM, HITACHI H7650, 120 kV). The peroxidase-like activity of the iron nanoparticles was tested in a mixture of 500 μl NaOAc buffer (0.1 M, pH 4.5) containing 20 μg CAT-NPs, 1% $H_2O_2$ and 100 μg TMB. The blue color produced was recorded with a spectrophotometer at an absorbance of 652 nm. These conditions were also used for assaying the activity of CAT-NPs on biofilms. Two additional substrates, 3,3'-diaminobenzidine (DAB) and AMPLEX® UltraRed (Thermo-Fisher Scientific; 568/581 nm), were also used under the same reaction conditions to confirm the activity of the CAT-NPs. Chemicals and materials were supplied by Sigma-Aldrich unless otherwise specified.

Biofilms were formed on saliva-coated hydroxyapatite (sHA) surfaces (tooth enamel-like material) using *Streptococcus mutans*, a well-established biofilm-forming, acidogenic and matrix-producing oral pathogen (FIG. 9). The hydroxyapatite discs (surface area, 2.7±0.2 cm$^2$) were purchased from Clarkson Chromatography and the bacteria strain, *Streptococcus mutans* UA159, was purchased from ATCC. The biofilm method is based on the saliva-coated hydroxyapatite (sHA) disc model (see Xiao et al., *PLoS Pathog.* 2012; Klein et al., *J Vis Exp.* 2011; Falsetta et al., *Infect Immun.,* 2014; Koo et al., *J Bacteriol,* 2010; Koo et al., *J Antimicrob Chemother,* 2003). The hydroxyapatite discs were coated with filter-sterilized, clarified whole saliva and vertically suspended in 24-well plates using a custom-made wire disc holder (FIG. 9), which was designed to mimic the free smooth surfaces of the teeth (Klein et al., *J Vis Exp.* 2011). *S. mutans* UA159 cells were grown in ultra-filtered (10-kDa cutoff; Millipore, Billerica, Mass.) tryptone-yeast extract (UFYTE) broth containing 1% sucrose at 37° C. and 5% $CO_2$ to mid-exponential phase. Each sHA disc was placed in 2.8 ml of UFYTE medium with 1% (w/v) sucrose containing an inoculum with a defined microbial population of *S. mutans* (10$^5$ CFU/ml), and incubated at 37° C. and 5% $CO_2$ for 19 h. The culture medium was replaced with fresh medium twice daily (at 19 h and 29 h) until the end of the experimental period (43 h). The biofilms were collected and analyzed at specific time points (19 h, 29 h and 43 h) by means of confocal fluorescence imaging, microbiological and biochemical analyses (Xiao et al., *PLoS Pathog.* 2012; Klein et al., *J Vis Exp.* 2011; Falsetta et al., *Infect Immun.,* 2014; Koo et al., *J Bacteriol,* 2010; Koo et al., *J Antimicrob Chemother,* 2003).

Figure 10A:
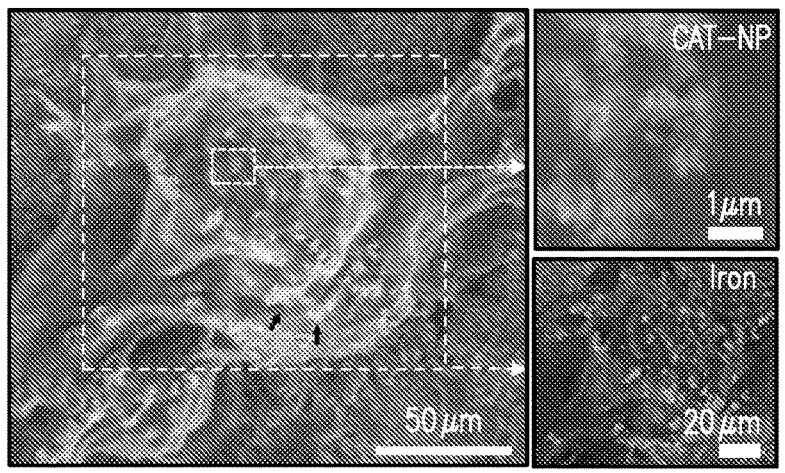
Figure 10B:
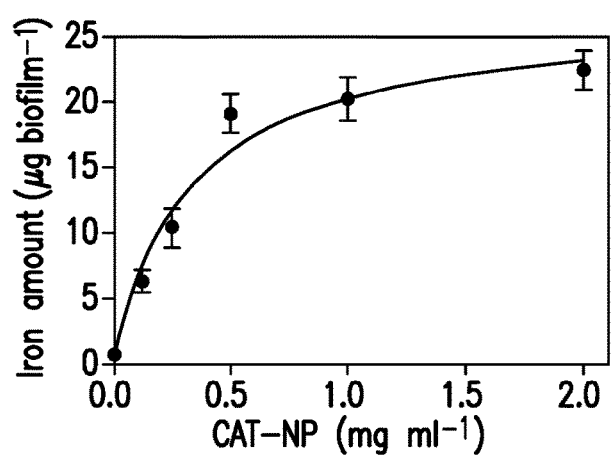

To mimic a pathogenic situation, biofilms were formed in the presence of sucrose, which provides a substrate for exopolysaccharides (EPS) synthesis and acid production (pH values reaches 4.5-5.0 in this biofilm model, consistent with plaque pH at diseased sites in humans) (Koo et al., *J Dent Res.* 2013). Scanning electron microscopy (FIG. 10A1), energy dispersive spectroscopy (EDS) (FIG. 10A2) and inductively coupled plasma optical emission spectrometry (ICP-OES) (FIG. 10B) all demonstrated that CAT-NPs bind to biofilms. The maximum binding of CAT-NPs to biofilms was achieved at a concentration of 0.5 mg/ml (FIG. 10B).

Quantitative assessment of CAT-NP binding within biofilms was performed with inductively coupled plasma optical emission spectrometry (ICP-OES). Briefly, biofilms were treated with CAT-NPs (0, 0.125, 0.25, 0.5, 1 or 2 mg/ml) in 0.1 M NaOAc (pH 4.5) for 5 or 10 min at room temperature at specific time-points (FIG. 9). The biofilms were removed from the sHA discs and homogenized via standard water bath sonication followed by probe sonication (Xiao et al., *PLoS Pathog,* 2012). The suspension was centrifuged and the biofilm pellet was washed twice with water to remove unbound material. The pellet was then dissolved with 250 μl Aqua regia ($HCl/HNO_3$=3:1) at 60° C. overnight (Naha et al., *J Mater. Chem. Biol. Med.,* 2014). Then, 4.75 ml Milli-Q water was added and the sample was analyzed by ICP-OES for iron content. In a separate experiment, intact biofilms were examined with environmental SEM and the amount of iron was analyzed via energy dispersive spectroscopy (EDS) on the same SEM.

To determine the retention and the spatial distribution of CAT-NPs within an intact biofilm 3D architecture, multiphoton confocal microscopy and computational analysis were used (Xiao et al., *PLoS Pathog.* 2012; Klein et al., *J Vis Exp,* 2011; Koo et al., *J Bacteriol,* 2010). The exopolysaccharides (EPS) (in red) were labeled using 1 Alexa Fluor 647-labeled dextran conjugate (10 kDa; 647/668 nm; Molecular Probes Inc., Invitrogen Corp., Carlsbad, Calif., USA) and the bacterial cells (in green) were stained with 2.5 μM SYTO 9 (485/498 nm; Molecular Probes Inc.). The CAT-NPs (in white) were detected via their inherent non-linear optical property using multiphoton confocal microscopy (Xiao et al., *PLoS Pathog,* 2012; Klein et al., *J Vis Exp,* 2011; Liao et al., *Adv Funct Mater,* 2013; Koo et al., *J Bacteriol,* 2010; Liao et al., *Adv Funct Mater,* 2013). Imaging was performed using a Leica SP5 multiphoton confocal microscope with a 20× LPlan N (1.05 numerical aperture) water immersion objective lens. The excitation wavelength was 780 nm and the emission wavelength filter used for detecting SYTO 9 was a 495/540 OlyMPFC1 filter, while the filter used for detecting Alexa Fluor 647 was an HQ655/40M-2P filter. The excitation wavelength for the CAT-NPs was 910 nm, which does not excite SYTO 9 or Alexa Fluor 647. The confocal images were analyzed using software for simultaneous visualization and quantification of EPS, bacterial cells and CAT-NPs within the intact biofilms. The Amira 5.0.2 software platform (Mercury Computer Systems Inc., Chelmsford, Miss.) was used to create 3D renderings of each component (EPS, bacteria and CAT-NPs) within the biofilms for visualization of the 3D architecture. COMSTAT and ImageJ were used for quantitative analysis as previously described (Xiao et al., *PLoS Pathog.* 2012; Klein et al., *J Vis Exp.* 2011; Koo et al., *J Bacteriol,* 2010).

As shown in FIG. 10C, in situ imaging revealed that the CAT-NPs were effectively retained throughout the biofilm structure following topical treatments. Quantitative analysis across the biofilm thickness (from top to bottom) showed that most of the nanoparticles were found at a depth between 25 and 150 μm, where both EPS and bacterial biomass are most abundant (FIG. 10D).

To investigate whether the CAT-NPs attached to biofilms were capable of rapidly catalyzing $H_2O_2$ at acidic pH (pH 4.5) to produce free radicals in situ, a colorimetric method using 3,3',5,5'-tetramethylbenzidine (TMB) was used (Gao et al., *Nat Nanotechnol.* 2007). The nanoparticles that were bound to the biofilms catalyzed the reaction of TMB (which serves as a peroxidase substrate) in the presence of $H_2O_2$ to produce a blue color (FIG. 10E) as a result of free radical generation. The blue color has a maximum absorbance at 652 nm. The experiment was repeated using an additional peroxidase substrate (di-azo-aminobenzene) to further confirm the presence of peroxidase-like activity in CAT-NP treated biofilms (FIG. 11).

Figure 10E:
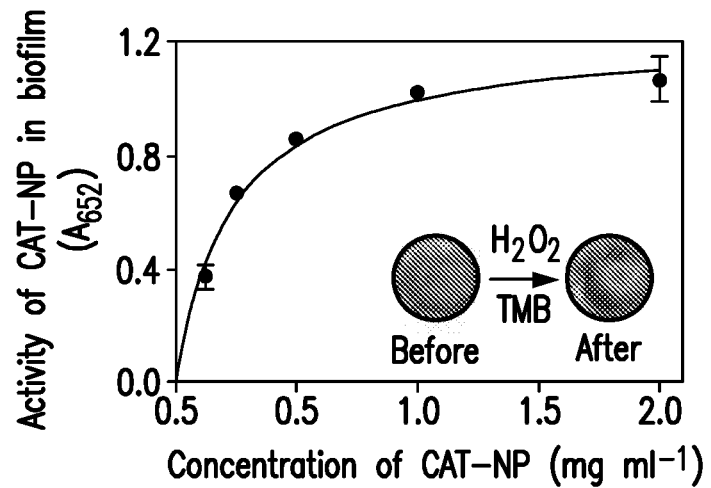
Figure 10F:
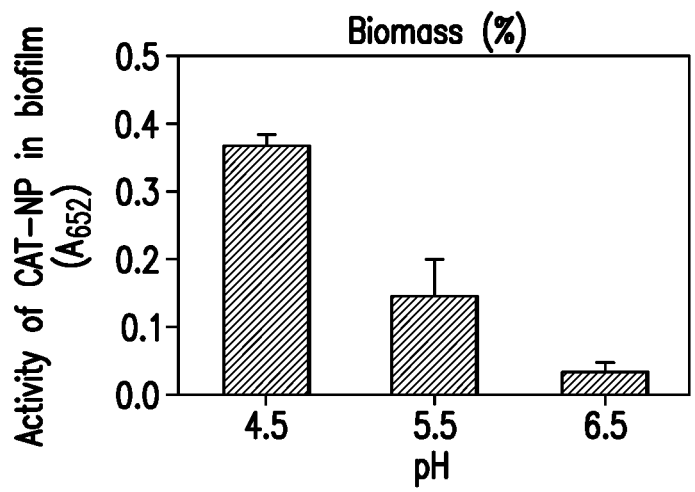
Figure 11:
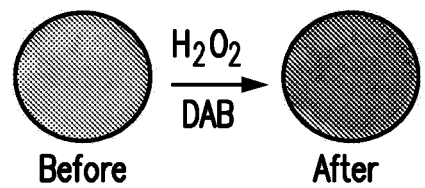
FIG. 11 depicts images showing the activity of CAT-NPs bound within biofilms using another peroxidase substrate (3,3'-diaminobenzidine; DAB). The brown color indicates free-radical generation via $H_2O_2$ catalysis.
Figure 12:
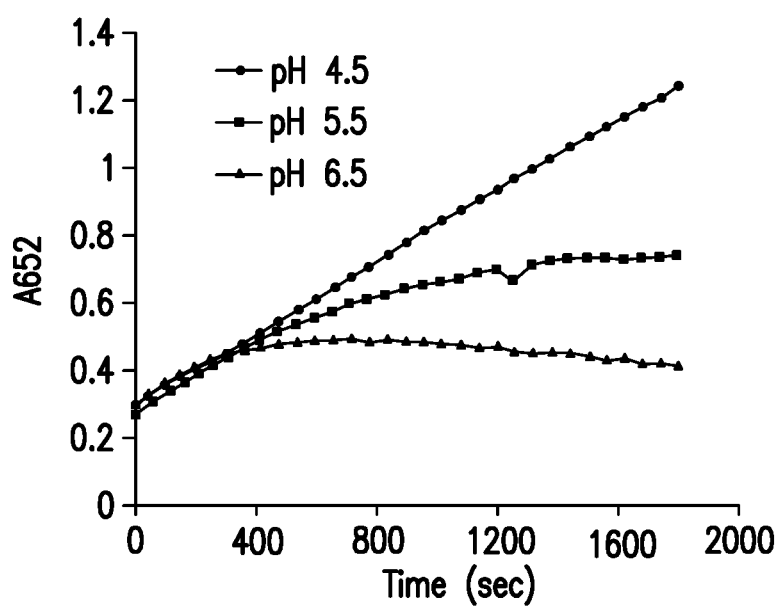
FIG. 12 is a graph showing the catalytic activity of CAT-NPs bound within biofilms at different pH values, as measured by a 3,3',5,5'-tetramethylbenzidine (TMB) reaction.

Consistent with the amount of CAT-NPs adsorbed within the biofilm, the highest catalytic activity was achieved at concentrations between 0.5 to 2.0 mg/ml under the tested conditions (FIG. 10E). $H_2O_2$ catalysis by CAT-NPs depends on pH (Gao et al., *Nat Nanotechnol,* 2007); therefore, the peroxidase-like activity of the biofilm-bound CAT-NPs was measured in buffers with pH values ranging from 4.5 to 6.5. As shown in FIG. 10F, CAT-NPs attached to biofilms exert greater catalytic efficiency at acidic pH (4.5-5.5), which is congruent with the pH values found in pathological conditions (Mercier et al., *J Antimicrob Chemother,* 2002; Poschet et al. *Trends Mol Med,* 2002; Fejerskov et al., *J Dent Res,* 1992). These data show that CAT-NPs were retained within biofilms following brief topical applications and displayed pH-responsive catalysis of $H_2O_2$ in situ.

To investigate whether CAT-NP-mediated $H_2O_2$ catalysis and generation of free-radicals in situ can kill embedded bacteria and degrade the EPS-matrix within biofilms, the following experiments were performed. To assess the antibiofilm efficacy of CAT-NP/$H_2O_2$ combination, four treatments were prepared: Control (0.1 M NaOAc, pH 4.5), CAT-NP alone (0.5 mg/ml in 0.1 M NaOAc, pH 4.5), 1% $H_2O_2$ (0.1 M NaOAc, pH 4.5), CAT-NP+$H_2O_2$ (0.5 mg/ml CAT-NP with 1% $H_2O_2$ in 0.1 M NaOAc, pH 4.5). Biofilms treated with CAT-NPs (0.5 mg/ml) were immediately exposed to $H_2O_2$ (0.1 to 1%, v/v) and the number of viable cells and EPS content were determined (FIG. 13A and FIG. 14).

The sHA discs and biofilms were topically treated with each of the solutions for 5 or 10 min, washed 3 times with sterile saline (0.89% NaCl) to remove unbound material and then transferred to culture medium (FIG. 9). The first treatment was applied directly after salivary pellicle formation (sHA) and the treated sHA discs were then transferred to a culture medium containing *S. mutans* ($10^5$ CFU/ml). Biofilms were allowed to form on the sHA discs for 6 h, at which point a second treatment was applied. The next day, biofilms were treated twice daily (at 19 h and 29 h). At the end of experimental period (43 h), the total number of viable cells in each biofilm was assessed by counting the number of colonies formed (Koo et al., *J Bacteriol,* 2010; Klein et al., *J Vis Exp,* 2011; Koo et al., *J Antimicrob Chemother,* 2003). For CFU and dry weight assessment, biofilms were removed from sHA discs and homogenized via standard sonication that does not kill bacterial cells, while providing maximum recoverable viable counts. Aliquots of the homogenized biofilm suspension were serially diluted and plated onto blood agar plates and, after a 48 h incubation, the colonies were visually counted. The remaining biofilm suspension was washed twice with Milli-Q $H_2O$, oven-dried (into pre-weighed foil boats) for 2 h and weighed.

Figure 13A:
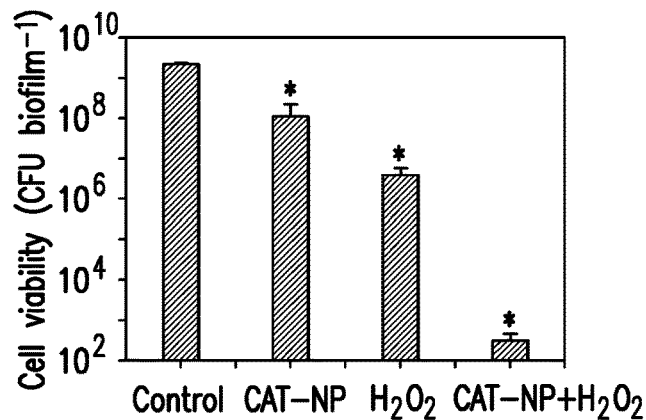
FIGS. 13A-13D depict the bacterial killing, EPS degradation and biofilm disruption achieved by the combination of CAT-NPs and $H_2O_2$.
Figure 14B:
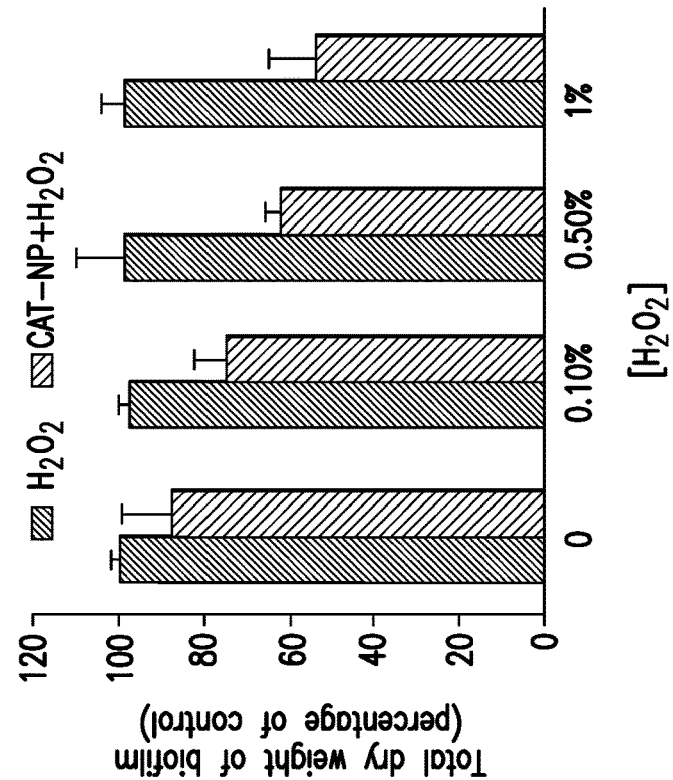
FIGS. 14A-14B depict graphs showing the anti-biofilm activity of CAT-NPs with different concentrations of $H_2O_2$.
Figure 14A:
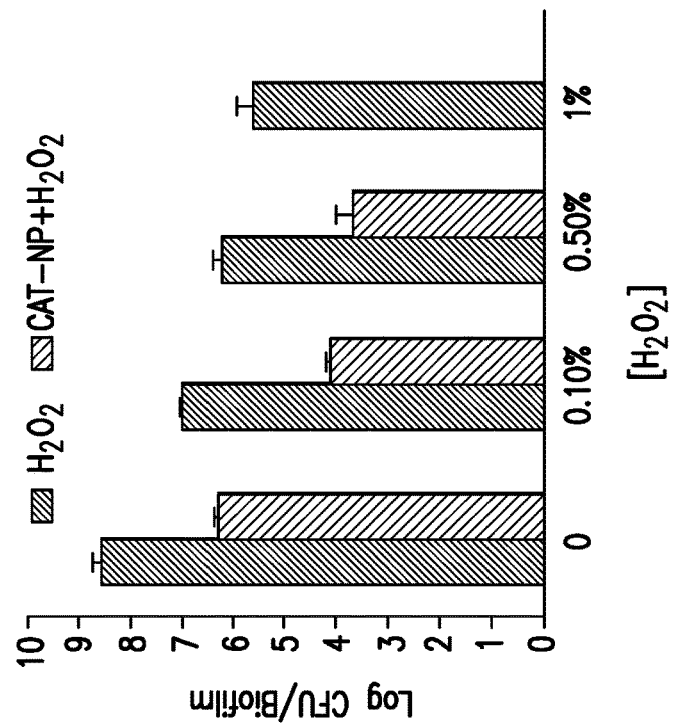

As shown in FIG. 13A and FIG. 14, there is an exceptionally strong biocidal effect against *S. mutans* within biofilms, with the killing of >99.9% of the bacteria in 5 minutes. CAT-NPs in combination with 1% $H_2O_2$ exposure caused a >5-log reduction in the number of viable cells compared to control biofilms or CAT-NP-treated biofilms without $H_2O_2$ (FIG. 13A). As shown in FIG. 13A, the combination of CAT-NPs and $H_2O_2$ was >5,000-fold more effective in killing *S. mutans* than $H_2O_2$ alone, indicating a clear synergistic effect between CAT-NPs and $H_2O_2$ to potentiate the killing efficacy of the agents.

Given that free-radicals produced from $H_2O_2$ catalysis can also degrade polysaccharides in vitro (Gao et al., *Nanoscale,* 2014), the amount of EPS in the CAT-NP-treated biofilms was analyzed following exposure to $H_2O_2$. For assessment of EPS degradation, 100 μg of (insoluble or soluble) glucans produced by purified glucosyltransferases (GtfB or GtfD) (Koo et al., *Antimicrob Agents Chemother,* 2002) were mixed with each of the treatment solutions (in 0.1 M NaOAc, pH 4.5) and incubated at 37° C. for 30 min. The glucans were manufactured as follows. Each of the Gtf enzymes (10 U) were mixed with a sucrose substrate buffer (100 mM sucrose, 20 μM dextran 9,000, 50 mM KCl, 1.0 mM $KPO_4$, 1.0 mM $CaCl_2$ and 0.1 mM $MgCl_2$, pH 6.5) and incubated for 4 h at 37° C. After incubation, the glucans produced were collected by centrifugation, washed and the total amounts were determined by standard phenol-sulfuric acid colorimetric assay (Koo et al., *J Antimicrob Chemother,* 2003; Koo et al., *Antimicrob Agents Chemother,* 2002). One hundred micrograms of glucan was mixed with each of the treatment solutions (total reaction volume of 300 μl in 0.1 M NaOAc, pH 4.5) and incubated at 37° C. for 30 min with rocking. After incubation, the amount of reducing sugars was determined by Somogyi-Nelson colorimetric assay.

Figure 13B:
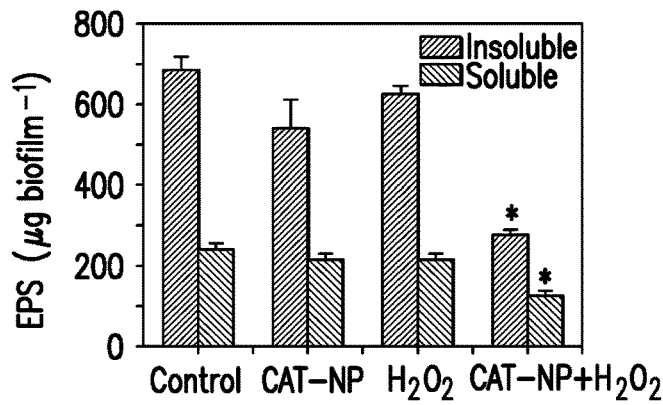
Figure 13C:
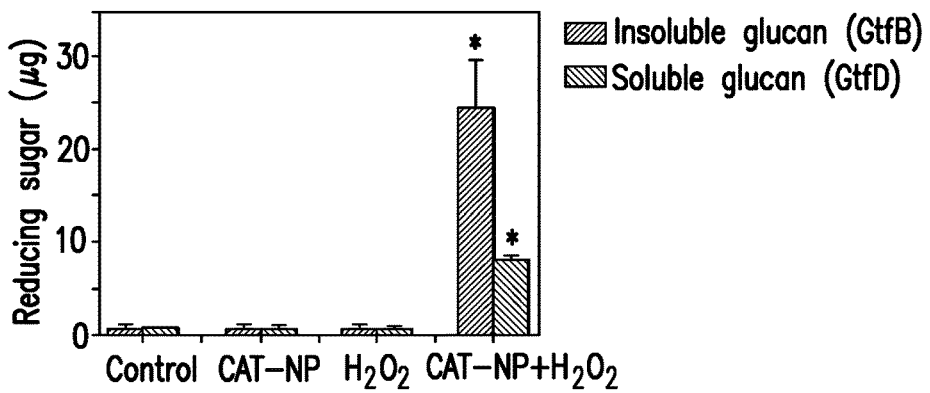

As shown in FIG. 13B, the amounts of insoluble and, to a lesser extent, soluble EPS were significantly reduced in the presence of CAT-NPs and $H_2O_2$ compared to the control or compared to treatments with $H_2O_2$ or CAT-NPs alone. Insoluble EPS are comprised primarily of α1,3-linked glucans, while soluble EPS are mostly α1,6-linked glucans, and both are produced (Bowen and Koo, *Caries Res,* 2011). Therefore, further analysis was performed to determine whether purified extracellular glucans produced by GtfB (which synthesizes α1,3-linked glucans) and GtfD (α1,6-linked glucans) are degraded following incubation with CAT-NP in the presence or absence of $H_2O_2$. FIG. 13C shows that both glucans (particularly from GtfB) were broken down as determined by measuring the amount of glucose released from the polysaccharide following CAT-NP/$H_2O_2$ treatment. In contrast, $H_2O_2$ alone or CAT-NPs alone failed to cleave either glucan, an observation consistent with their inability to reduce EPS within biofilms. The degradation of insoluble EPS is highly relevant because glucans or comparable polysaccharides form the core of many matrices in other biofilms (Flemming and Wingender, *Nat Rev Microbiol*, 2010; Koo et al., *J Dent Res.* 2013), and are associated with dental caries and other biofilm-related maladies (Hall-Stoodley et al., *Nat Rev Microbiol*, 2004; Flemming and Wingender, *Nat Rev Microbiol*, 2010; Lebeaux et al., *Microbiol Mol Biol Rev,* 2014; Koo et al., *J Dent Res,* 2013; Bowen and Koo, *Caries Res,* 2011). Collectively, the in vitro data suggest that the combination of CAT-NP with $H_2O_2$ could significantly suppress virulent biofilms.

Figure 13D:
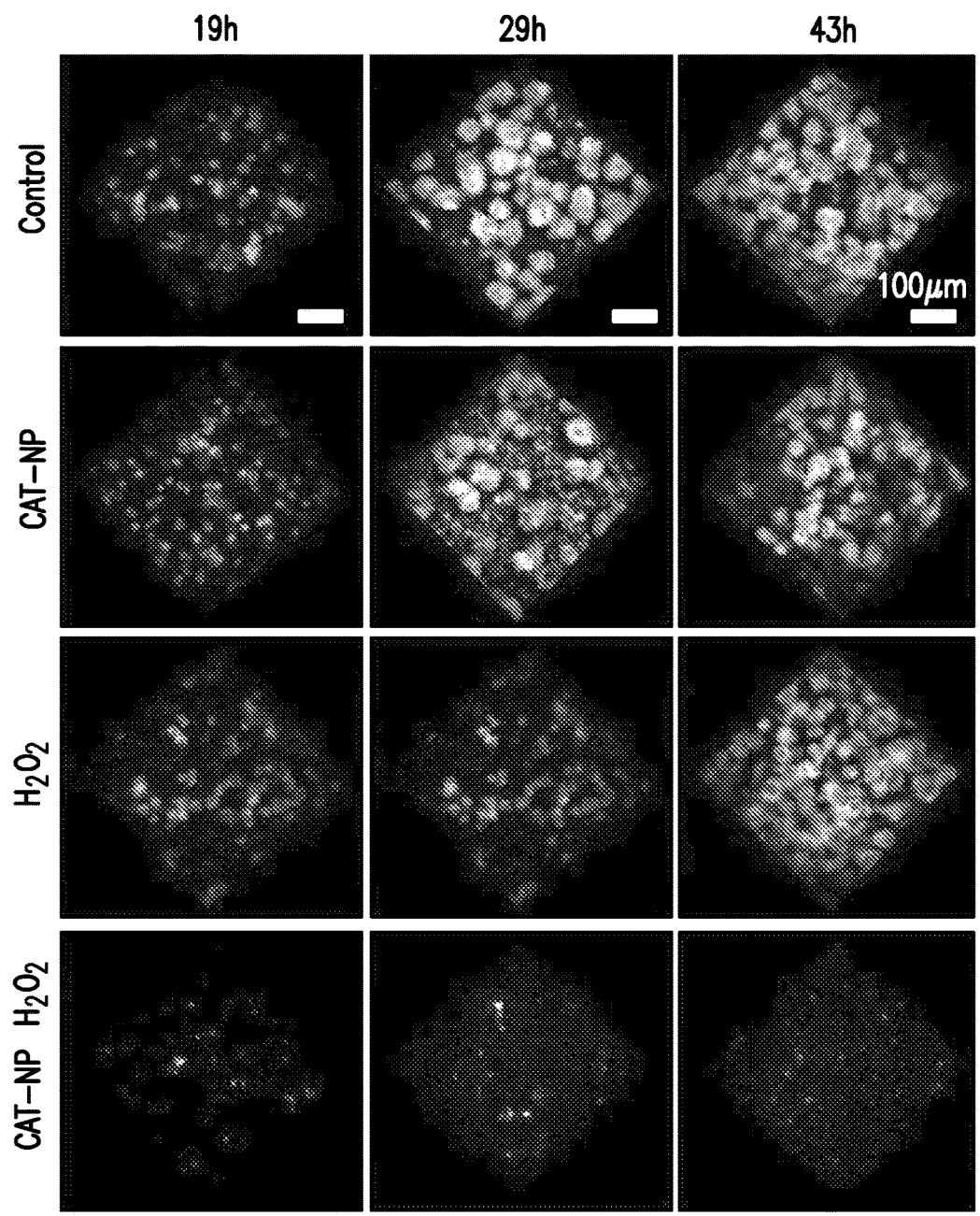

Since it was shown that CAT-NPs are retained within biofilms and catalyze $H_2O_2$ in situ for enhanced biofilm disruption, a clinically feasible combination therapy was developed, that includes topical treatment with CAT-NPs (at 0.5 mg/ml) immediately followed by $H_2O_2$ (at 1%, w/v) exposure (CAT-NP/$H_2O_2$), twice daily. This treatment regimen was initially tested in vitro to assess whether biofilms could be disrupted by CAT-NPs in combination with $H_2O_2$. Confocal microscopy imaging revealed that treatments with CAT-NP/$H_2O_2$ impaired both the accumulation of bacterial cells (in green) and the development of EPS-matrix (in red) (FIG. 13D and FIG. 15). In contrast, topical treatments with CAT-NPs or $H_2O_2$ alone had limited anti-biofilm effects in vitro, consistent with synergistic potentiation when these agents are used in combination.

Example 3

To test the in vivo efficacy of CAT-NP/$H_2O_2$ and to determine whether CAT-NP/$H_2O_2$ could suppress the onset and severity of dental caries in vivo, a rodent model of the disease was used (Bowen, *Odontology,* 2013; Falsetta et al., *Infect Immun,* 2014; Horev et al., *ACS Nano,* 2015).

In brief, animal experiments were performed on a well-established rodent model of dental caries (Bowen, *Odontology,* 2013; Falsetta et al., *Infect Immun,* 2014; Horev, *ACS Nano,* 2015; Koo et al., *J Dent Res,* 2005). Briefly, Sprague-Dawley rats, 15 days old, were purchased with their dams from Harlan Laboratories (Madison, Wis., USA) and screened for infection with *S. mutans*. Any animals infected with *S. mutans* prior to inoculation were removed from the study. The animals were then infected orally using an actively growing (mid-logarithmic) culture of *S. mutans* UA159 and their infection was checked via oral swabbing. Infected animals were randomly placed into four treatment groups (12 animals/group) and their teeth were treated topically using a custom-made applicator twice daily. The treatment groups included: (1) Control (0.1 M NaOAc, pH 4.5), (2) CAT-NPs only (0.5 mg/ml in 0.1 M NaOAc, pH 4.5), (3) 1% $H_2O_2$ (0.1 M NaOAc, pH 4.5), (4) CAT-NP+ $H_2O_2$ (0.5 mg/ml CAT-NP with 1% $H_2O_2$ in 0.1 M NaOAc, pH 4.5). Agents were applied topically (orally-delivered; 100 µL per rat) twice-daily for 3 weeks, with brief exposures (30 s) to simulate clinical use.

Each group was provided with the National Institutes of Health cariogenic diet 2000 and 5% sucrose water ad libitum. The experiment proceeded for 3 weeks. All animals were weighed weekly and their physical appearance was noted daily. All animals gained weight equally among the experimental groups and remained in good health during the experimental period. At the end of the experimental period, the animals were sacrificed and the jaws were surgically removed and dissected. All of the jaws were defleshed and the teeth were prepared for caries scoring according to Larson's modification of Keyes' system disease (see Larson, *Animal models in cariology: symposium and workshop proceedings special supplement of microbiology abstracts,* 1981; Bowen, *Odontology,* 2013; Falsetta et al., *Infect Immun,* 2014; Horev, *ACS Nano,* 2015). Determination of the caries score of the codified jaws was performed by one calibrated examiner. Furthermore, both the gingival and palatal tissues were collected and processed for hematoxylin and eosin (HE) staining for histopathological analysis.

Figure 16B:
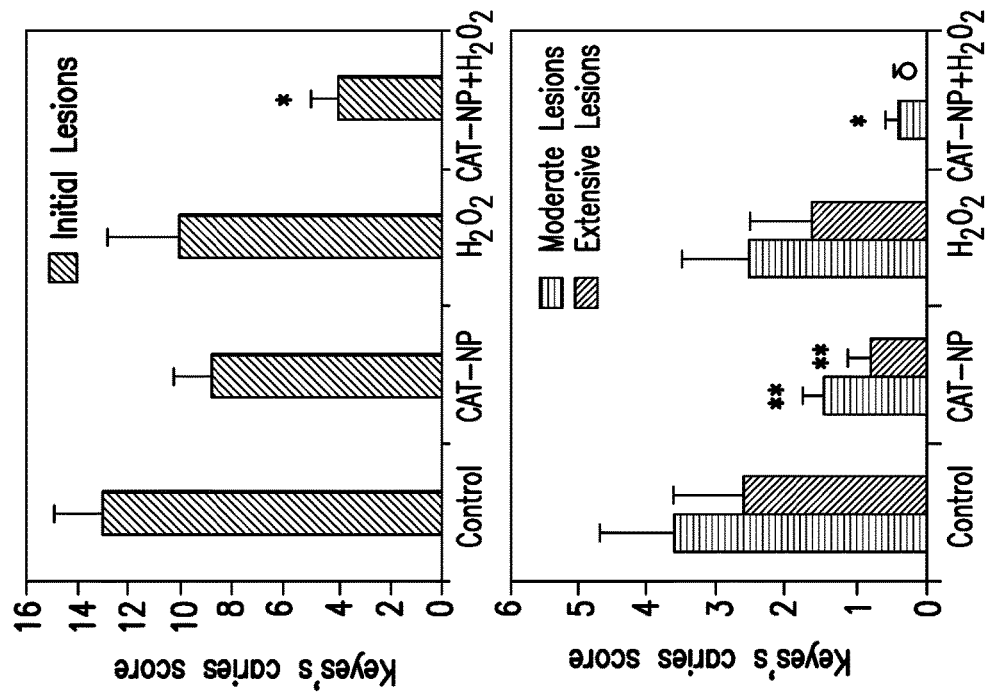
FIGS. 16A-16B depict images and graphs illustrating the protection against development of carious lesions by CAT-NP/$H_2O_2$ treatment.
Figure 16A:
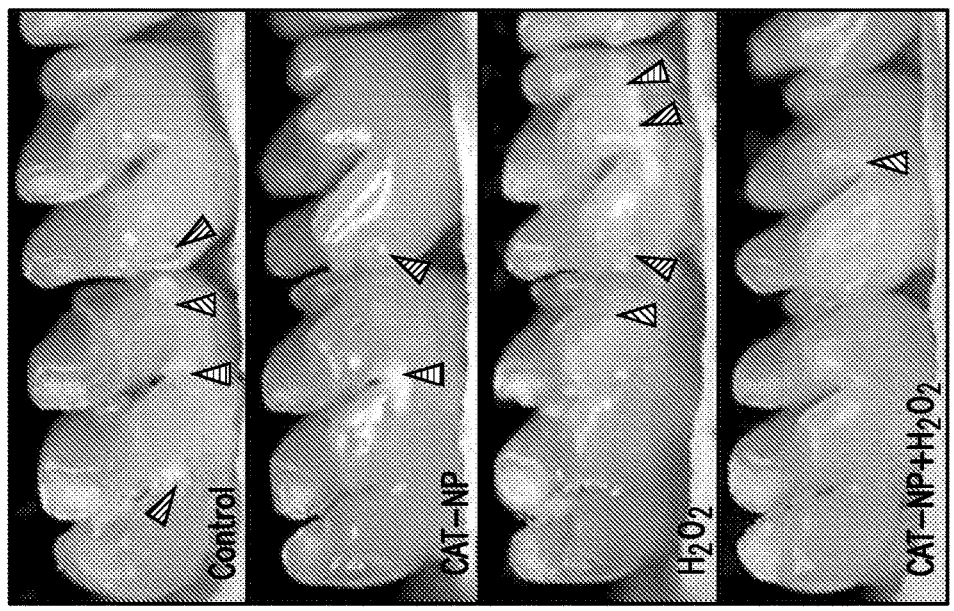
Figure 17:
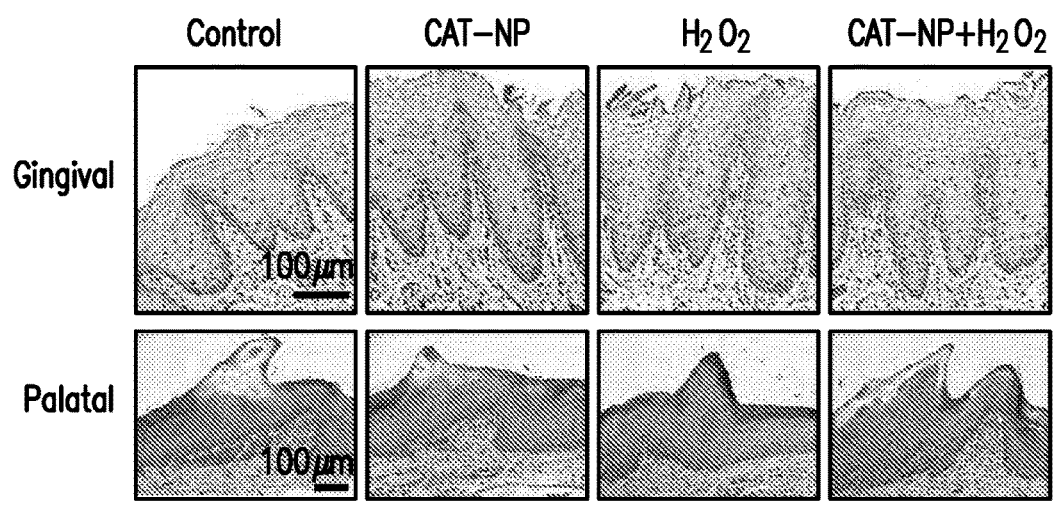
FIG. 17 depicts histopathology images of gingival and palatal tissue in animals treated with CAT-NP and/or $H_2O_2$, showing no cytotoxic effects and devoid of any cell abnormalities following topical treatments for 3 weeks.

In this animal model, teeth progressively developed carious lesions (analogous to those observed in humans), proceeding from initial areas of enamel demineralization (FIG. 16A, green arrow) to further destruction (blue arrows), leading to the most severe lesions characterized by cavitation (red arrow). The effects of CAT-NP/$H_2O_2$ treatments on caries development were striking. Quantitative caries scoring analyses revealed that CAT-NP/$H_2O_2$ significantly attenuated both the initiation and severity of the lesions (vs. vehicle control; FIG. 16B) and completely blocked extensive enamel damage, thereby preventing the onset of cavitation. In sharp contrast, treatments with $H_2O_2$ alone were without significant effect, while treatment with CAT-NPs alone showed some reduction of the severity of carious lesions (vs. vehicle-control; FIGS. 16A and 16B). The excellent cariostatic effect of CAT-NP/$H_2O_2$ provides compelling evidence of in vivo efficacy in a clinically-relevant model. Additionally, no deleterious effects were observed on rats that received topical applications of CAT-NP/$H_2O_2$. In particular, histopathological analysis of gingival and palatal tissues from CAT-NP/$H_2O_2$-treated animals showed no sign of cytotoxic effects, such as proliferative changes, inflammatory responses and/or necrosis, when compared to untreated (or vehicle-treated) animals (FIG. 17).

Figure 18A:
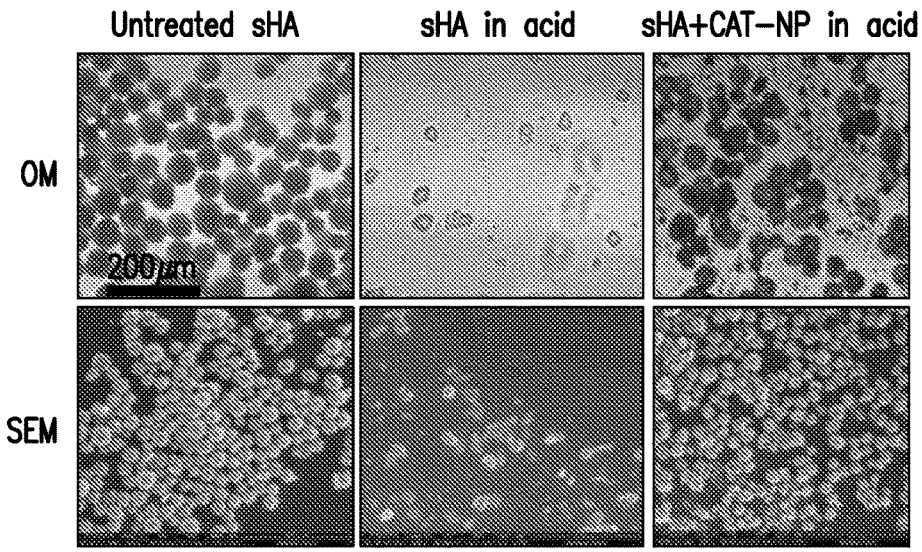
FIGS. 18A-18C depict images, graphs and illustrations of the reduction of sHA acid-dissolution by CAT-NP treatment.

Treatment with CAT-NPs alone reduced the severity of caries lesions to some extent, as indicated above. Without being bound to a particular theory, iron ions appear to inhibit dental caries by interfering with the enamel demineralization process, in addition to antibacterial effects of the iron ions (Rosalen et al., *Arch Oral Biol,* 1996; Pecharki et al., *Caries Res,* 2005; Delbem et al., *Caries Res,* 2012; Ribeiro et al., *Braz Oral Res,* 2012). Iron ions can be rapidly released from CAT-NPs when incubated at acidic pH (4.5) within minutes, but not at pH 7.0 (FIG. 18A).

To investigate whether CAT-NPs could reduce apatitic acid-dissolution by releasing iron at acidic pH, the following saliva-coated HA beads acid-dissolution and iron release assays were used. Hydroxyapatite (Bio-Rad Laboratories) beads were coated with filter-sterilized clarified whole saliva to obtain saliva-coated hydroxyapatite (sHA) (Koo et al., *Antimicrob Agents Chemother,* 2002; Gregoire et al., *Appl Environ Microbiol,* 2011; Ambatipudi et al., *J Proteome Res,* 2010). For sHA acid-dissolution assay, 10 mg of sHA beads were incubated in 1 ml of 0.1 M NaOAc buffer (pH 4.5) containing 0.5 mg/ml CAT-NP for 2 h with rocking at room temperature. Then, the supernatant was removed and sHA beads were resuspended again in 1 ml of fresh acidic NaOAc buffer and incubated as described above; this process was repeated 6 times. The same procedure was conducted with sHA beads without CAT-NP (control). An aliquot of sHA immediately before and after acid-dissolution was taken and analyzed via optical microscopy (OM) and SEM. In parallel, the remaining sHA beads were collected by centrifugation, oven-dried and weighed for the determination of their dry-weight. The remaining dry-weight of the sHA treated with CAT-NPs was compared to the control group to evaluate the efficiency of the CAT-NPs to reduce demineralization. For iron release assay, 0.5 mg/ml of CAT-NPs was incubated in 0.1 M NaOAc (pH 4.5) at room temperature for 0, 3, 5, 10, 30, 60, 120 min. The mixture was centrifuged at 10,000 g for 5 min and the supernatant was collected for iron concentration measurement using an Iron Assay Kit (Sigma-Aldrich)

according to the manufacturer's protocol. As a control, the amount of iron released in 0.1 M NaOAc (pH 7) was determined using the same procedure indicated above.

Figure 18B:
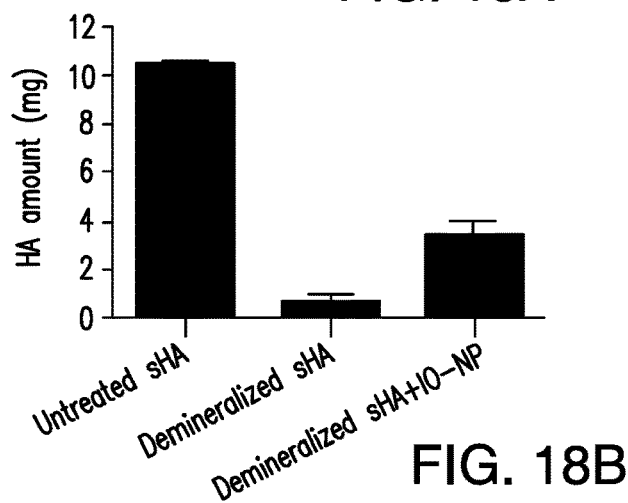
Figure 18C:
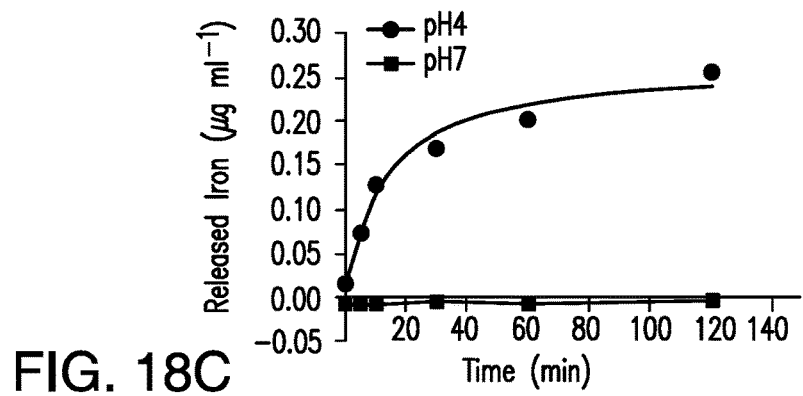

FIGS. 18B and 18C show graphs of saliva-coated hydroxyapatite (sHA) beads that were incubated in acidic sodium acetate buffer (pH 4.5) with or without CAT-NP, and then examined via SEM and analyzed to determine the amount of sHA remaining after acid incubation. As shown in FIG. 18B, sHA beads that were not treated with CAT-NPs were almost completely dissolved. In contrast, acid-dissolution of sHA was reduced in the presence of CAT-NP (FIG. 18B). These findings suggest that CAT-NPs may provide an additional mechanism of caries prevention by reducing apatite acid-dissolution. Statistical analyses for the experimental data above were performed using SAS 9.5 (SAS Institute) (Falsetta et al., *Infect Immun*, 2014).

Current therapeutic approaches, including antibacterial nanoparticles, are primarily focused on inhibiting the activity or killing the bacteria without addressing the presence of the protective biofilm matrix and acidic microenvironments, which can limit their efficacy against infections caused by biofilms (Lebeaux et al., *Microbiol Mol Biol Rev*, 2014; Allaker and Memarzadeh, *Int J Antimicrob Agents*, 2014).

Figure 19A:
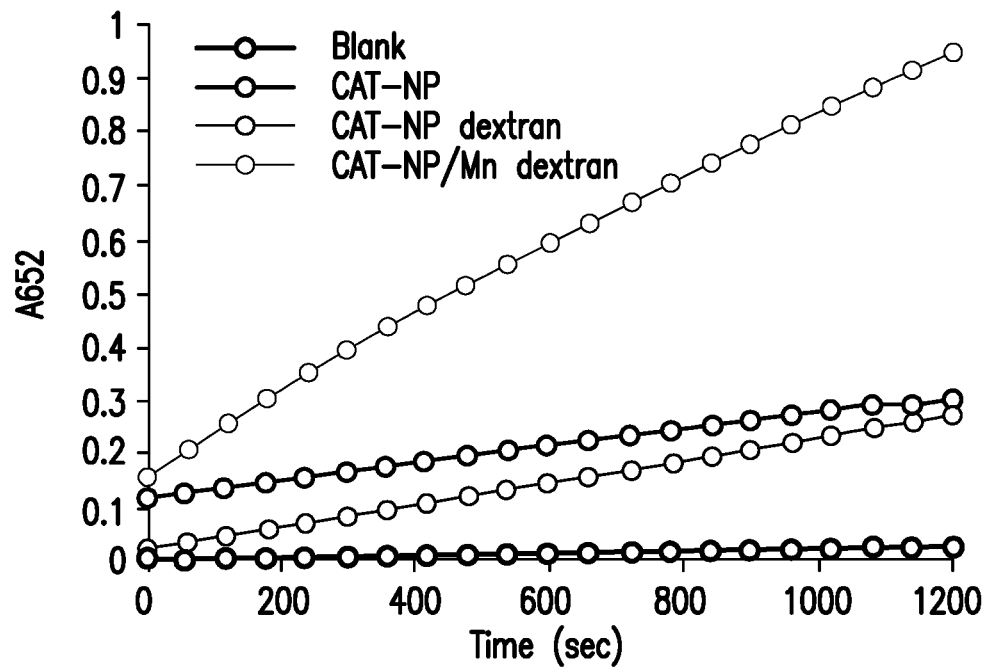
FIGS. 19A-19B depict graphs showing the comparison of the catalytic activities of modified CAT-NPs.

The present disclosure presents evidence on how nanoparticles can be exploited to combat a biofilm-associated disease in a clinically-relevant in vivo model. FIG. 1 summarizes a biocompatible and pH-responsive strategy that contains 4 major properties: (1) CAT-NPs are retained within 3D biofilm structure after brief topical exposure; (2) CAT-NPs rapidly catalyze $H_2O_2$ at acidic pH to produce free radicals in situ that simultaneously (3) degrade EPS; and (4) kill bacteria embedded within biofilms. In addition, CAT-NPs release iron ions at acidic pH that reduce apatite demineralization, which may be of a potential value for biofilm-associated bone diseases (Katsarelis et al., *J Dent Res*, 2015; Arciola et al, *Adv Exp Med Biol*, 2015). CAT-NPs could suppress the development of a common biofilm-associated disease, while sparing normal tissues in vivo. CAT-NPs can be synthesized with low cost at large scale, while the flexibility of CAT-NP chemistry can lead to the development of additional nanocrystal cores that can further improve catalysis performance (FIG. 19). Thus, this approach could lead to a feasible new platform for development of anti-biofilm therapeutics based on nanocatalysts for topical use against oral diseases and other human infections as well as industrial and naval biofouling.

Example 4

This Example uses the flexibility of IO-NP synthesis chemistry to further enhance the retention, catalytic activity and demineralizing-blocking effects of IO-NPs, so that the effectiveness of the IO-NP/$H_2O_2$ system for biofilm control in vitro can be optimized.

Different metal salts (such as $MnCl_2$) can be incorporated into the IO-NP structure to enhance the rate and level of $H_2O_2$ catalysis by the nanoparticles. Furthermore, IO-NPs can be coated with variations of biocompatible dextran with the purpose of enhancing retention of the IO-NPs at the tooth/biofilm interface and within the biofilm. Amorphous calcium phosphate can be added into the IO-NPs to improve the effects against enamel demineralization at acidic pH. The efficacy of optimized IO-NPs can be assessed in vitro and the most effective nanoparticles (vs. current IO-NP) can be selected for further evaluation.

In this Example, a small library of novel nanocrystal cores with surface coatings of dextran (for enhanced retention) and varying dopant materials (for enhanced catalysis) was produced. The data discussed below demonstrates that these modifications are feasible and can enhance the efficacy of the disclosed therapeutic approach. Different IO-NPs and doped IO-NP formulations are shown in Table 1 below. The dextran-coated iron oxide nanoparticles shown in Table 1 were synthesized as previously disclosed (Naha et al., *J Mater Chem Biol Med*, 2014). In brief, 12.5 g of dextran (MW 10,000) were dissolved in 25 ml of deionized (DI) water. The resulting solution was placed in an ice bath and purged with nitrogen gas for 30 minutes while stirred to completely remove oxygen from the flask. For each formulation, 980 mg of ferric chloride and 360 mg of ferrous chloride were added to the dextran solution. 15 ml of concentrated ammonium hydroxide was added to the dextran-iron solution using a syringe pump over 6 hr. The nanoparticle suspension was then heated to 90° C. for an hour and then stirred at room temperature overnight. The resulting nanoparticle suspension was centrifuged at 20 k rcf for 30 min to remove aggregates. The IO-NP-containing supernatant was collected, concentrated to 15 ml and washed with citrate buffered saline using 100 kDa MW diafiltration columns. IO-NPs coated with differing unmodified dextran molecular weights (1, 5, 10, 20 and 40 kDa) were synthesized.

TABLE 1

Synthesis and characterization of dextran coated IO-NP and doped IO-NP formulations.

| Different IONP and doped IONP Formulations | Hydrodynamic diameter (nm) | Zeta potential (mV) | ICP-OES Fe (mg/ml) | (mg/ml) |
|---|---|---|---|---|
| IONP_T10 | 35 ± 0.25 | −18 ± 2 | 6.8 | 0 |
| IONP_T1.5 | 49 ± 1.2 | −17 ± 2 | 5.4 | 0 |
| IONP_T40 | 49 ± 0.5 | −10 ± 1.5 | 4.2 | 0 |
| FeMn_T10 | 45 ± 0.2 | −21 ± 1 | 5.2 | 0.29 (Mn) |
| FeCo_T10 | 49 ± 0.15 | −18 ± 0.5 | 5.8 | 0.31 (Co) |
| FeNi_T10 | 30 ± 0.5 | −14 ± 2.5 | 5.4 | 0.17 (Ni) |

Although the newly developed nanoparticles are novel, they are based on materials that are highly biocompatible and are already clinically approved as MM contrast agents (Fan et al., *Wires Nanomed Nanobi*, 2013). The dopant metals have been shown to enhance catalytic activity of IO-NPs (e.g., $MnCl_2$) and are found in the body. Additionally, the nanoparticles can be synthesized on a large scale and the end product would be highly affordable. Therefore, the potential of the disclosed system for clinical use is significant.

Figure 20:
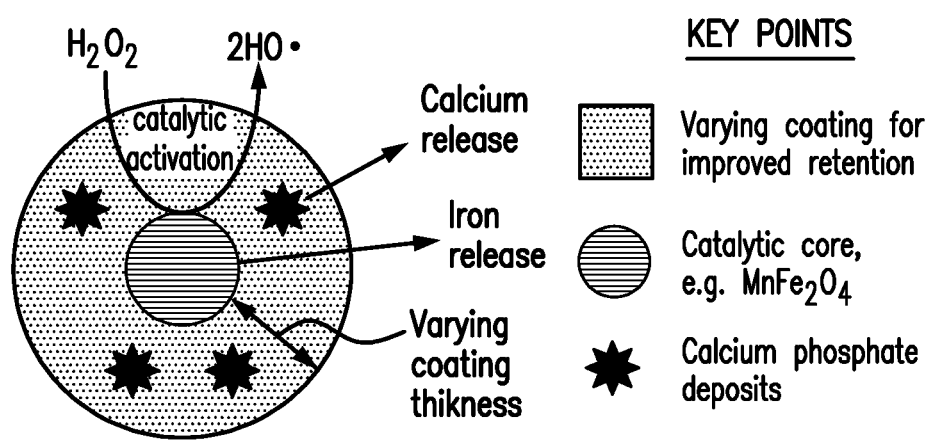
FIG. 20 illustrates potential modifications that can optimize the effectiveness of the IO-NPs.

The iron oxide nanoparticles are based on the dextran-coated iron oxide nanoparticles approved for use in patients, such as Feridex, Combidex and Feraheme (Wang, *Quantitative imaging in medicine and surgery*, 2011). These iron oxide nanoparticles are regarded as highly biocompatible because they breakdown into harmless, naturally occurring substances (i.e., iron and sugar molecules) (Tassa et al., *Accounts of chemical research*, 2011; Koo et al., *Journal of bacteriology*, 2010). To improve and optimize the platform, the effects of making the following 3 modifications the effect of coating, core doping and including calcium phosphate, can be investigated (FIG. 20).

To investigate the effect the coating has on the activity of the IO-NPs, dextran-coated iron oxide nanoparticles can be synthesized as disclosed above (Naha et al., *J Mater Chem*

Figure 19B:
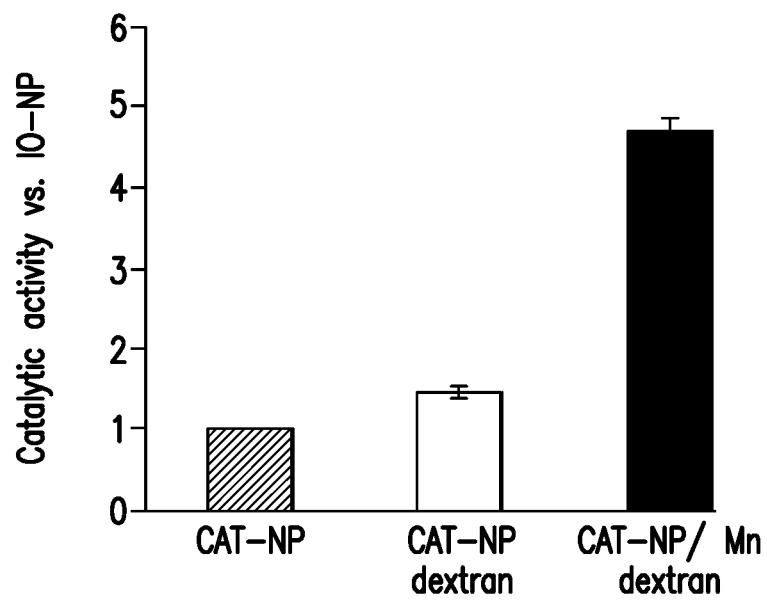

*Biol Med*, 2014). IO-NPs coated with differing unmodified dextran molecular weights (1, 5, 10, 20 and 40 kDa) or modified dextran (e.g., aminated, cross-linked, carboxy and diethylaminoethyl) are synthesized. Also, the clinically available formulation Feraheme is studied. Varying the dextran coating type can alter the access of $H_2O_2$ to the nanoparticle surface, which can then alter the catalytic performance. The effect the IO-NP coating has on the catalysis of $H_2O_2$ was determined using the previously mentioned TMB assay. FIG. 19B (light gray bar) shows that dextran coated iron oxides catalyzed the activation of hydrogen peroxide and that dextran is the biocompatible coating that offered the catalytic activity closest to the IO-NPs that did not have a coating. Furthermore, various types of dextran coatings can potentially enhance IO-NP retention at tooth/biofilm interfaces and within EPS-rich cariogenic biofilms. Previous studies have shown that exogenous dextran can be used as primers for EPS synthesis by *S. mutans*-derived glucosyltransferases (Gtfs) present on tooth-pellicles, which, in turn, can be incorporated into the matrix during biofilm initiation (Xiao et al., *PLoS pathogens*, 2012; Bowen and Koo, *Caries research*, 2006; Koo et al., *Journal of dental research*, 2013) without affecting catalytic activity (Gao et al., *Nat Nanotechnol*, 2007). Furthermore, retention can be enhanced via glucan-to-glucan adhesive interactions (FIG. 21) (Xiao et al., *PLoS pathogens*, 2012; Bowen and Koo, *Caries research*, 2011; Koo et al., *Journal of dental research*, 2013; Banas and Vickerman, *Critical reviews in oral biology and medicine: an official publication of the American Association of Oral Biologists*, 2003).

To investigate the effect of IO-NP core doping with a metal, the following methods can be used. Syntheses are performed where varying percentages of dopant metal salts such as $MnCl_2$, $CoCl_2$ and $NiCl_2$ (1, 5, 10 and 20%, or more) are included in the cores. The addition of dopant metals is a strategy to improve the performance of catalysts (Mohamed et al., *Mat Sci Eng R*, 2012; Bin Asif et al., *Nanoscale research letters*, 2014; Wang et al., *Journal of Molecular Catalysis a-Chemical*, 2013). Twenty % Mn-doped dextran-coated IO-NPs were synthesized and the inclusion of Mn was confirmed by inductively coupled plasma mass spectrometry (ICP-MS). FIG. 19B shows that the rate of hydrogen peroxide activation was increased 4.7 fold compared to undoped IO-NPs. Through this process, cores can be developed that have radically improved catalytic performance compared with the original IO-NPs, e.g., IO-NPs that do not have a doped core.

IO-NPs can be modified by the inclusion of calcium phosphate as an additive to improve demineralization-blocking effects (and possibly enhance remineralization) of the nanoparticles. Calcium phosphate can be included in IO-NPs by mixing IO-NP solutions with calcium nitrate and then adding potassium phosphate dropwise in a 1.67:1 Ca:P ratio (Sun et al., *J Res Natl Inst Stan*, 2010; Liou et al., *Biomaterials*, 2004). Variations can be synthesized by altering the ratio of IO-NP to calcium phosphate. The effect of calcium phosphate on the blocking of demineralization, IO-NP retention and on $H_2O_2$ catalysis can be examined. Alternatively, calcium can be included by doping as described above or by use of reverse microemulsion synthesis methods (Kong et al., *Curr Appl Phys*, 2005). In addition, should the inclusion of calcium phosphate markedly adversely affect the catalytic activity of the nanoparticles, calcium phosphate nanoparticles (CP-NPs) can be separately made and a mixture of IO-NPs and CP-NPs can be applied. These IO-NPs can be characterized for size by means of transmission electron microscopy (TEM, FEI Tecnai T12), dynamic light scattering (DLS) and for zeta potential (Zetasizer ZS90, Malvern Instruments), while concentration can be determined using ICP-MS (Naha et al., *J Mater Chem*, 2014). These analyses ensure standardized size and concentration of the nanoparticles. Optimization of these different parameters can be performed using the assays described below and IO-NPs that combine the best features identified, e.g., a doped core with an altered coating that includes calcium phosphate, can then be synthesized.

Figure 21:
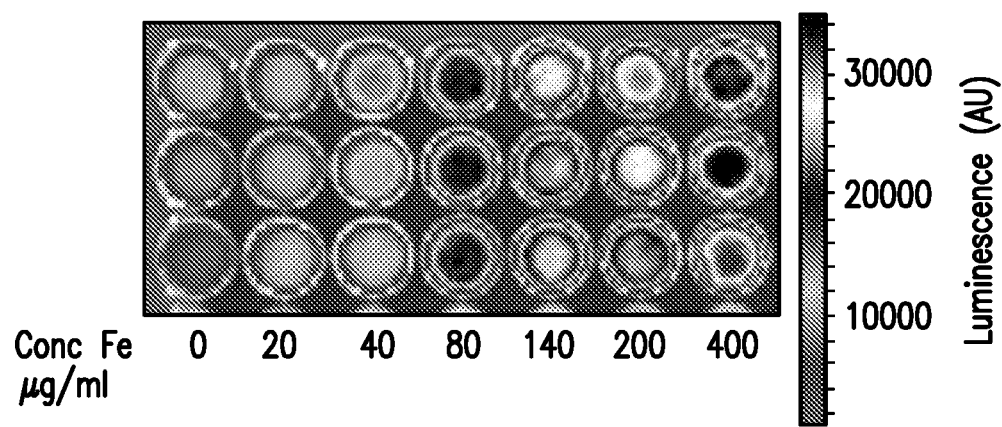
FIG. 21 is an image showing in vitro catalysis of $H_2O_2$ by dextran-coated IO-NPs, as evidenced by light production from luminol.

For assessment of the catalytic activity and bioactivity of the modified IO-NPs, the following methods can be used. The ability of the nanoparticles to function as catalysts for $H_2O_2$ activation is assessed via the measurement of luminescence intensity over time using a luminol assay. In brief, the nanoparticles are mixed with hydrogen peroxide and luminol for up to 10 minutes, where hydrogen peroxide reacts on the iron oxide nanoparticle surface to produce radicals that activates luminol to produce light (Triantis et al., *Chem Eng J*, 2008). FIG. 21 shows data from a luminol assay. The best catalysts yield the strongest light emissions. The luminol assay is also complemented with an established colorimetric method using 3,3',5,5'-Tetramethylbenzidine (TMB) as substrate. TMB generates a blue color with a specific absorption at 652 nm after reacting with free radicals catalyzed by IO-NP over time (Gao et al., *Nat Nanotechnol*, 2007). All nanoparticles are tested under the same conditions to compare their activity (i.e., 0.5 mg/ml and 0.5% $H_2O_2$, as used previously) in terms of catalytic rate and level. Screening is performed in adsorption buffer (that mimics the ionic strength of saliva) and clarified human whole saliva (to simulate biological environment) (Horev et al., *ACS nano*, 2015). For subsequently selected lead nanoparticle candidates, different IO-NP and $H_2O_2$ concentration combinations can be tested to achieve maximum effectiveness at a minimal dose.

Figure 22A:
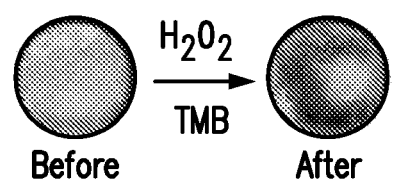
FIGS. 22A-22B depict the catalytic activity of IO-NPs bound to biofilms.
Figure 22B:
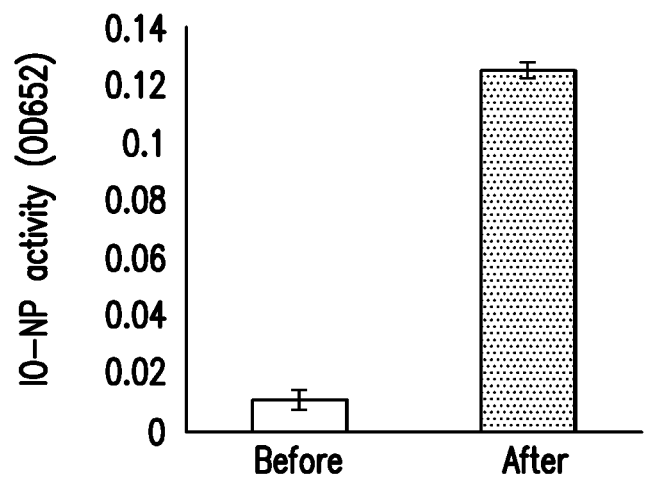

For the IO-NP retention assays, the following methods can be used. Retention of nanoparticles within biofilms are assessed using a saliva-coated hydroxyapatite biofilm model. Topical application is used with brief exposures (1 or 5 min) of each IO-NP (0.5 mg/ml) twice-daily to simulate a clinical treatment regimen. Topically treated biofilms are washed to remove unbound or loosely bound IO-NP. Then, the biofilms are removed and homogenized (Bowen and Koo, *Caries research*, 2011; Koo et al., *J Antimicrob Chemoth*, 2003). The amount of IO-NPs retained within a biofilm is determined by analyzing the iron content of the biofilm by inductively coupled plasma mass spectroscopy (ICP-MS) (Naha et al., *J Mater Chem B*, 2014). The catalytic activity of $H_2O_2$ (0.5%) is measured via colorimetric (TMB) assay (Gao et al., *Nat Nanotechnol*, 2007) to ensure that the IO-NPs bound within biofilms are active (FIG. 22).

The bacterial killing effects of the IO-NPs in the presence of $H_2O_2$ can be evaluated using the same biofilm model and topical treatment disclosed above. IO-NP-treated biofilms are exposed to $H_2O_2$ and the dry-weight and the total viable cells of *S. mutans* are determined using standard culturing and qPCR-based methods (Cury and Koo, *Analytical biochemistry*, 2007; Klein et al., *Mol Oral Microbiol*, 2012). In this model, up to 72 biofilms can be formed simultaneously in a single experiment; thus, facilitating the screening of newly developed IO-NPs.

In addition, the ability of IO-NPs to degrade glucans via oxidative cleavage in the presence of $H_2O_2$ can be determined according to the following method. Briefly, insoluble and soluble glucans (produced by *S. mutans* Gtfs) are used. One hundred micrograms of either insoluble or soluble glucans are incubated with IO-NPs and $H_2O_2$ under the same conditions to compare their activity and the amount of breakdown products (i.e., glucose) can be measured using standard colorimetric methods (Koo et al., *J Antimicrob Chemoth*, 2003; Kopec et al., *Glycobiology*, 1997).

The demineralization-blocking effects of the nanoparticles can be analyzed by measuring the amount of acid dissolution of saliva-coated HA beads and saliva-coated tooth-enamel (sTE) slabs in the presence or absence of IO-NPs. Briefly, sHA beads or sTE slabs are incubated in sodium acetate buffer (pH 4.5) for 4 h at 37° C. The sHA beads are centrifuged and washed three times to remove dissolved apatite and the amount of calcium and phosphate are measured using ICP-MS and colorimetric assays (Naha et al., *J Mater Chem B*, 2014). The remaining sHA beads (non-dissolved) are collected for the determination of the dry-weight. The sTE slabs (after treatment) are analyzed for the amount of demineralization using the highly standardized surface microhardness (SMH) method (Arthur et al., *Journal of oral diseases*, 2014; Hara et al., *Caries research*, 2005; Zero et al., *Journal of dental research*, 1992; Hara et al., *European journal of oral sciences*, 2014; Cury et al., *Caries research*, 1997). Briefly, enamel SMH is measured using a hardness tester connected to a motorized micrometer stage. A Knoop diamond is used that is under a 50 g load and 11 s dwell time. Enamel SMH is determined by measuring the length of the indentations (μm) using a dedicated image analysis system at baseline (before treatment) and after treatment and then calculated as the % SMH change, which is directly associated with the level of demineralization.

Figure 23A:
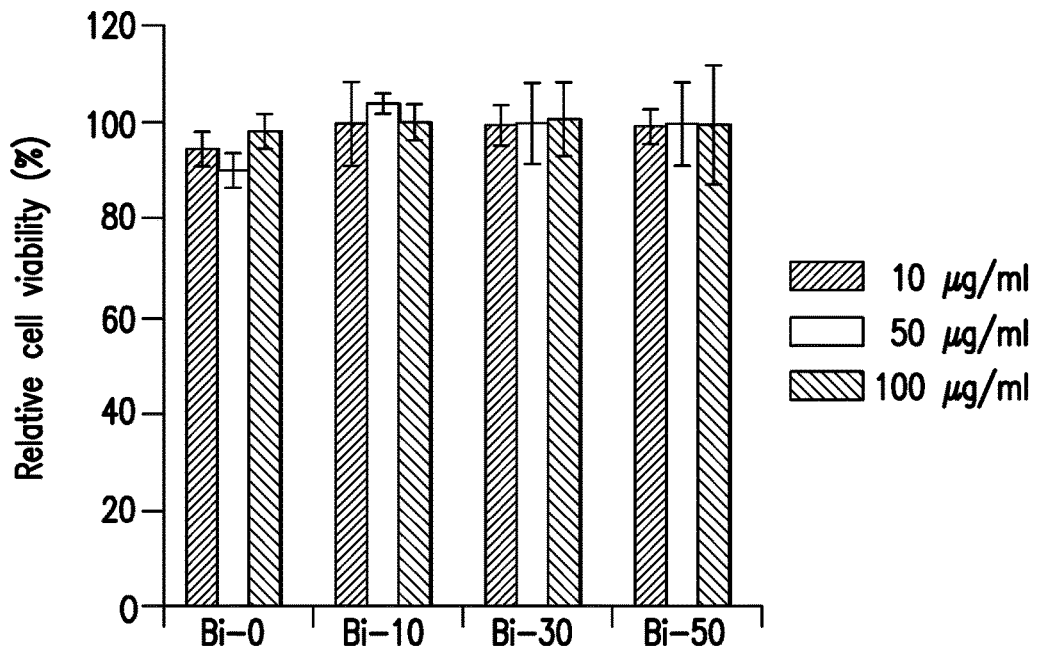
FIGS. 23A-23B depicts cell viability after incubation with iron oxide nanoparticles for 24 hours.
Figure 23B:
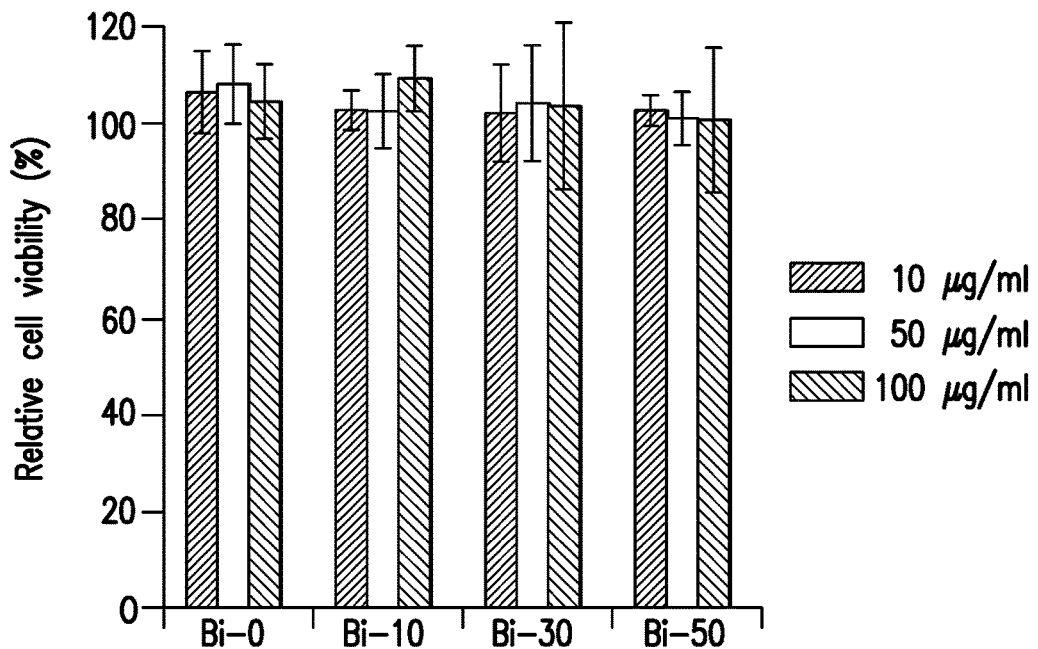

For the in vitro assessment of biocompatibility, the following methods can be used. The system can include IO-NPs and $H_2O_2$ that are biocompatible and approved for clinical use. Furthermore, the concentrations used are lower than currently used in the clinical setting and the contact of the IO-NPs with bystander tissues will be minimal due to the short-term, topical application of the treatment. In vivo data showed that twice-daily exposure of IO-NP/$H_2O_2$ combination did not cause cytotoxic effects. However, evaluation of the potential cytotoxicity of the optimized nanoparticles (with or without $H_2O_2$) can be performed using oral (gingival and mucosal) epithelial and fibroblast cells to ensure that there are no effects on the viability of mammalian cells. In brief, biocompatibility can be assessed by exposing the cells to nanoparticles alone or in combination with $H_2O_2$ for up to 10 minutes (to mimic topical exposure). A range of IO-NP concentrations (10-1000 μg/ml) and $H_2O_2$ (0.5-1% v/v) are evaluated and MTS or MTT assays are performed to determine cell viability using standard protocols (Naha et al., *J Mater Chem B*, 2014). This assay can be complemented with qualitative observations of cells under microscopy. Incubations over a range of timeframes (1-10 minutes) and pulse-chase experiments can be performed, where cells are incubated with IO-NPs for 10 min and are then followed over time and their viability is measured at 24, 72 and 168 hr. FIG. 23 shows the biocompatibility of dextran-coated IO-NPs. The comprehensive screening can ensure the selection of the most effective and biocompatible IO-NPs for cariogenic biofilm control and the prevention of dental caries.

Further optimization of the IO-NP characteristics can be performed to improve catalytic activity and bioactivity by taking advantage of IO-NP chemistry flexibility. A variety of novel nanoparticles that can catalyze the activation of $H_2O_2$ can be synthesized. Catalysts that activate hydrogen peroxide at rates of over one thousand-fold higher than the uncatalyzed rate can be identified. Also, different doped iron oxide nanoparticles can be generated to study for their catalytic properties (Cormode et al., *Contrast Media Mol Imaging*, 2014; Naha et al., *J Mater Chem B*, 2014). If difficulties arise, the synthesis of the IO-NPs can be altered by using different ratios of dopant metal salts, different dopant metals (e.g., Mg, Ca) and different coatings such as dopamine or phosphate-based ligands.

The present disclosure is well adapted to attain the ends and advantages mentioned as well as those that are inherent therein. The particular embodiments disclosed above are illustrative only, as the present disclosure can be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above can be altered or modified and all such variations are considered within the scope and spirit of the present disclosure.

Various publications, patents and patent application are cited herein, the contents of which are hereby incorporated by reference in their entireties.

The invention claimed is:

1. A method of treating an oral disease comprising:
   (i) administering to a subject an effective amount of a composition comprising one or more iron nanoparticles; and
   (ii) administering to the subject an effective amount of hydrogen peroxide.

2. The method of claim 1, wherein the composition further comprises a compound selected from the group consisting of fluoride, copper, calcium phosphate, sodium percarbonate and combinations thereof.

3. A method of treating an oral disease comprising administering to a subject an effective amount of a composition comprising one or more iron nanoparticles, wherein the one or more iron nanoparticles comprise nanoparticles conjugated to one or more enzymes selected from the group consisting of matrix degrading enzymes, peroxide producing enzymes and combinations thereof.

4. A method of treating a biofilm-associated disease comprising administering to a subject an effective amount of a composition comprising one or more iron nanoparticles, wherein the one or more iron nanoparticles comprise nanoparticles that have a polymeric coating.

5. The method of claim 1, wherein the hydrogen peroxide is administered in a solution that comprises hydrogen peroxide at a concentration from about 0.1% to about 3.0%.

6. A method of treating an oral disease comprising administering to a subject an effective amount of a composition comprising one or more iron nanoparticles, wherein the concentration of the iron nanoparticles within the composition is from about 0.01 to about 10.0 mg/ml.

7. A method for the elimination and/or treatment of an oral disease comprising:
   (i) contacting a surface having a biofilm with an effective amount of a composition comprising one or more iron nanoparticles; and
   (ii) contacting the surface with a solution comprising hydrogen peroxide,
   wherein the one or more iron nanoparticles and hydrogen peroxide react to form one or more radicals that eliminates and/or treats the oral disease.

8. The method of claim 1, wherein the one or more iron nanoparticles comprise nanoparticles that have a polymeric coating.

9. The method of claim 1, wherein the concentration of the iron nanoparticles within the composition is from about 0.01 to about 10.0 mg/ml.

10. The method of claim 1, wherein the one or more iron nanoparticles are doped with a metal or a salt thereof.

11. The method of claim 1, wherein the one or more iron nanoparticles comprise nanoparticles conjugated to one or more enzymes selected from the group consisting of matrix degrading enzymes, peroxide producing enzymes and combinations thereof.

12. The method of claim 1, wherein the oral disease comprises dental caries.

13. The method of claim 7, wherein the hydrogen peroxide is administered in a solution that comprises hydrogen peroxide at a concentration from about 0.1% to about 3.0%.

14. The method of claim 7, wherein the one or more iron nanoparticles comprise nanoparticles that have a polymeric coating.

15. The method of claim 7, wherein the concentration of the iron nanoparticles within the composition is from about 0.01 to about 10.0 mg/ml.

16. The method of claim 7, wherein the one or more iron nanoparticles are doped with a metal or a salt thereof.

17. The method of claim 7, wherein the one or more iron nanoparticles comprise nanoparticles conjugated to one or more enzymes selected from the group consisting of matrix degrading enzymes, peroxide producing enzymes and combinations thereof.

18. A method of treating a biofilm-associated disease comprising:
(i) administering to a subject an effective amount of a composition comprising one or more iron nanoparticles; and
(ii) administering hydrogen peroxide to the subject at a concentration from about 0.1% to about 3.0%.

19. The method of claim 18, wherein the hydrogen peroxide is present in the composition comprising the one or more iron nanoparticles.

20. The method of claim 18, wherein the composition further comprises a compound selected from the group consisting of fluoride, copper, calcium phosphate, sodium percarbonate and combinations thereof.

* * * * *